(12) United States Patent
Hanafusa

(10) Patent No.: US 9,308,530 B2
(45) Date of Patent: *Apr. 12, 2016

(54) REACTION CONTAINER PLATE AND REACTION TREATMENT APPARATUS

(75) Inventor: Nobuhiro Hanafusa, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 1807 days.

This patent is subject to a terminal disclaimer.

(21) Appl. No.: 12/529,536

(22) PCT Filed: Oct. 16, 2007

(86) PCT No.: PCT/JP2007/070127
§ 371 (c)(1),
(2), (4) Date: Sep. 1, 2009

(87) PCT Pub. No.: WO2008/108027
PCT Pub. Date: Sep. 12, 2008

(65) Prior Publication Data
US 2010/0028986 A1   Feb. 4, 2010

(30) Foreign Application Priority Data

Mar. 2, 2007  (JP) ................................. 2007-053471

(51) Int. Cl.
*C12M 1/34*  (2006.01)
*C12M 1/00*  (2006.01)
(Continued)

(52) U.S. Cl.
CPC ......... B01L 3/502738 (2013.01); B01L 3/5025 (2013.01); *B01J 2219/00315* (2013.01);
(Continued)

(58) Field of Classification Search
CPC ............ B01L 3/5025; B01L 3/502738; B01L 3/0268; B01L 2200/0605; B01L 2200/0684; B01L 2300/041; B01L 2300/046; B01L 2300/0829; B01L 2300/0864; B01L 2400/0478; B01L 2400/0481; B01L 2400/0487; B01L 2400/0605; B01L 2400/0611; B01L 2400/0622; B01L 2400/0644; B01J 2219/00315; B01J 2219/00391; B01J 2219/00364

USPC ..................... 435/287.2, 289.1; 422/188, 129
See application file for complete search history.

(56) References Cited

U.S. PATENT DOCUMENTS 6,391,623 B1 * 5/2002 Besemer et al. ........... 435/287.2
8,076,129 B2 * 12/2011 Hanafusa et al. .......... 435/289.1
(Continued)

FOREIGN PATENT DOCUMENTS

JP   2000-514928 A   11/2000
JP   2003-500205 A   1/2003
(Continued)

OTHER PUBLICATIONS

International Search Report for the Application No. PCT/JP2007/070127 mailed Mar. 18, 2008.

*Primary Examiner* — William H Beisner
*Assistant Examiner* — Danielle Henkel
(74) *Attorney, Agent, or Firm* — Cheng Law Group, PLLC

(57) ABSTRACT

Disclosed herein is a reaction container plate which prevents the entry of foreign matter from the outside and the pollution of an outside environment. A reaction container plate (1) includes a sealed reaction container (5), a reaction container channel (15) connected to the reaction container (5), a sealed container (17) provided separately from the reaction container (5), a sealed container channel (17a) connected to the sealed container (17), a syringe (33) for sending a liquid, a switching valve (47) for connecting the syringe (33) to the introduction channel (15) or the sealed container channel (17a), and a sealed container air vent channel (17b) of which one end is connected to the sealed container (17). When the syringe (33) is connected to the sealed container (17) via the switching valve (47) to inject a liquid contained in the syringe (33) into the sealed container (17) and to suck a liquid contained in the sealed container (17) into the syringe (33), a gas contained in the sealed container (17) is moved between the sealed container (17) and the sealed container air vent channel (17b).

25 Claims, 19 Drawing Sheets

(51) Int. Cl.
*B01J 19/00* (2006.01)
*B01J 10/00* (2006.01)
*B01L 3/00* (2006.01)
*B01L 3/02* (2006.01)
*G01N 35/00* (2006.01)

(52) U.S. Cl.
CPC ............... *B01J2219/00364* (2013.01); *B01J 2219/00391* (2013.01); *B01L 3/0268* (2013.01); *B01L 2200/0605* (2013.01); *B01L 2200/0684* (2013.01); *B01L 2300/041* (2013.01); *B01L 2300/046* (2013.01); *B01L 2300/0829* (2013.01); *B01L 2300/0864* (2013.01); *B01L 2400/0478* (2013.01); *B01L 2400/0481* (2013.01); *B01L 2400/0487* (2013.01); *B01L 2400/0605* (2013.01); *B01L 2400/0611* (2013.01); *B01L 2400/0622* (2013.01); *B01L 2400/0644* (2013.01); *G01N 2035/00277* (2013.01)

(56) References Cited

U.S. PATENT DOCUMENTS

| 2002/0045265 A1* | 4/2002 | Bergh et al. .................. 436/37 |
| 2005/0158213 A1 | 7/2005 | Tsudome et al. |
| 2006/0000709 A1 | 1/2006 | Bohm et al. |
| 2008/0069729 A1* | 3/2008 | McNeely .................... 422/63 |

FOREIGN PATENT DOCUMENTS

| JP | 3452717 B2 | 7/2003 |
| JP | 2004-163104 A | 6/2004 |
| JP | 2004-325462 A | 11/2004 |
| JP | 2005-114430 A | 4/2005 |
| JP | 2005-177749 A | 7/2005 |
| JP | 2005-199164 A | 7/2005 |
| JP | 2006-17719 A | 1/2006 |
| JP | 2006-29485 A | 2/2006 |
| JP | 2006-234590 A | 9/2006 |
| WO | WO-98/53311 A2 | 11/1998 |
| WO | WO-00/72968 A1 | 12/2000 |

* cited by examiner

REACTION CONTAINER PLATE AND REACTION TREATMENT APPARATUS

BACKGROUND OF THE INVENTION

1. Field of the Invention

The present invention relates to a reaction container plate suitable for use in various assays and analyses such as biological and biochemical assays, and general chemical analyses in the fields of medical care and chemistry, as well as a reaction processing apparatus for processing such a reaction container plate.

2. Description of the Related Art

As small reactors for use in biochemical assays or general chemical analyses, micro multi-chamber devices are used. Examples of such devices include micro container reaction container plates such as a microtiter plate constituted from a plate-shaped substrate having a plurality of containers formed in the surface thereof (see, for example, Japanese Patent Application Laid-open No. 2005-177749) and the like.

Further, as a structure for dispensing a small amount of liquid which can quantitatively treat a small amount of liquid, a structure having a first channel, a second channel, a third channel which is in communication with the first channel through an opening provided in the channel wall of the first channel, and a fourth channel which is in communication with the second channel through an opening provided in the channel wall of the second channel, connects one end of the third channel to the second channel, and has relatively lower capillary attraction than the third channel is developed (see, for example, Japanese Patent Application Laid-open Nos. 2004-163104 and 2005-114430). When such a structure for dispensing a small amount of liquid is used, a liquid introduced into the first channel is drawn into the third channel, and then the liquid remaining in the first channel is removed, and as a result the liquid having a volume corresponding to the capacity of the third channel is dispensed into the second channel.

SUMMARY OF THE INVENTION

Meanwhile, when a conventional micro container reaction container plate is used, the top surface of the reaction container plate is open to the atmosphere. Therefore, there is a possibility that foreign matter will enter a sample from outside or, on the other hand, a reaction product will pollute a surrounding environment.

Therefore, it is an object of the present invention to provide a reaction container plate which can prevent the entry of foreign matter from outside and the pollution of a surrounding environment, and a reaction processing apparatus using such a reaction container plate.

The present invention is directed to a reaction container plate including a sealed reaction container, a reaction container channel connected to the reaction container, a sealed container provided separately from the reaction container, a sealed container channel connected to the sealed container, a syringe for sending a liquid, a switching valve for connecting the syringe to the reaction container channel or the sealed container channel, and a sealed container air vent channel of which one end is connected to the sealed container.

When a liquid contained in the syringe is injected into the sealed container connected to the syringe via the switching valve, a gas contained in the sealed container is discharged into the sealed container air vent channel. On the other hand, when a liquid contained in the sealed container is sucked into the syringe, a gas flows into the sealed container through the sealed container air vent channel.

In the reaction container plate according to the present invention, a part of the sealed container air vent channel may be constituted from a narrow hole for maintaining the liquid-tightness of the sealed container in a state where there is no difference between the pressure in the sealed container and the pressure in the sealed container air vent channel.

The other end of the sealed container air vent channel may be hermetically sealed by being connected to a variable capacity part of which internal capacity is passively variable.

As one configuration example of the reaction container and the reaction container channel, the reaction container plate further including a container base constituted from a substrate and having the reaction container of which opening is provided in a surface of the substrate, a channel base provided on the surface of the container base so as to cover the reaction container to seal the reaction container and having a top surface, a back surface, and an introduction hole extending from the top surface to the back surface and located above the reaction container, and a channel cover provided on the channel base and having a hollow space in a surface thereof opposed to the channel base so that an introduction channel passing above the introduction hole is formed from the hollow space and the top surface of the channel base can be mentioned. In this case, the reaction container channel is constituted from the introduction channel and the introduction hole, the introduction channel can be hermetically sealed, the introduction hole does not allow the passage of a liquid at an introduction pressure applied to the inside of the introduction channel to introduce the liquid into the introduction channel but allows the passage of the liquid at an injection pressure much higher than the introduction pressure applied to the inside of the introduction channel to inject the liquid contained in the introduction channel into the reaction container, and the channel cover has a flexible part in at least a portion thereof corresponding to a part of the introduction channel so that after the liquid is introduced into the introduction channel, the flexible part of the channel cover is biased toward the channel base to apply the injection pressure to the inside of the introduction channel to inject the liquid into the reaction container through the introduction hole.

In such a configuration example, at least the introduction hole and a portion around the introduction hole in the channel base may be constituted from an elastic member so that the introduction hole is elastically closed to such a degree that it does not allow the passage of the liquid at the introduction pressure applied to the inside of the introduction channel but is elastically opened to such a degree that it allows the passage of the liquid at the injection pressure applied to the inside of the introduction channel.

A part of the introduction hole may have an inner diameter smaller than that of the introduction hole at the top surface of the channel base opposed to the channel cover.

In this case, the narrower part of the introduction hole may have an inner diameter of, for example, 1 μm to 2 mm.

The container base may have a plurality of the reaction containers. In this case, the introduction hole may be provided above each of the reaction containers, and the introduction channel may be provided to pass above the plurality of introduction holes.

The channel base may have a projecting portion which projects from a surface thereof opposed to the reaction container plate into the reaction container. In this case, the projecting portion may have a proximal end and a distal end narrower than the proximal end, and the introduction hole may be provided so as to pass through the projecting portion.

As another configuration example of the reaction container and the reaction container channel, the reaction container plate further including a reaction container air vent channel connected to the reaction container can be mentioned. In this case, the reaction container channel is constituted from a groove formed in the contact surface between two members bonded together or from the groove and a through hole formed in the member, and includes a main channel, a metering channel branched off the main channel and having a predetermined capacity, and an injection channel of which one end is connected to the metering channel and another end is connected to the reaction container. The main channel and the reaction container air vent channel can be hermetically sealed. The injection channel is formed narrower than the metering channel, and does not allow the passage of a liquid at a liquid introduction pressure applied to introduce the liquid into the main channel and the metering channel and at a purge pressure applied to purge the liquid from the main channel but allows the passage of the liquid at a pressure higher than the liquid introduction pressure and the purge pressure.

In such a configuration example, the contact angle of the injection channel with a water drop is, for example, 90° or larger, and the area of an interface between the injection channel and the metering channel is, for example, 1 to 10,000,000 $\mu m^2$.

The reaction container plate may have a plurality of the reaction containers. In this case, the metering channel and the injection channel may be provided for each of the reaction containers and the plurality of metering channels may be connected to the main channel.

A projecting portion may be provided so as to project from a top inner surface of the reaction container. In this case, the other end of the injection channel is located at the tip of the projecting portion. The projecting portion may have a proximal end and a distal end narrower than the proximal end.

In the reaction container plate according to the present invention, the sealed container may be a sample container for containing a sample liquid.

In this case, the sample container may be hermetically sealed with an elastic member which allows a dispensing device having a sharp tip to pass through to form a through hole and which also allows the through hole to be closed by pulling out the dispensing device due to its elasticity.

In this case, the sample container may previously contain a liquid for pretreating a sample or a reagent.

The reaction container plate according to the present invention may further include one or more reagent containers, each of which is constituted from the sealed container, other than the sample container. The reagent container may previously contain a reagent to be used for the reaction of a sample liquid and be sealed with a film, or may have an openable and closable cap so that the reagent can be injected thereinto. An example of the film for sealing the reagent container to prevent the leakage of a reagent includes one through which a dispensing device having a sharp tip can pass.

In a case where the reaction container plate according to the present invention is intended to be used for gene analysis, the reaction container plate preferably includes a gene amplification container which is constituted from the sealed container and used for carrying out gene amplification reaction. The gene amplification container preferably has a shape suitable for controlling a temperature according to a predetermined temperature cycle. It is noted that gene amplification can also be carried out also in the reaction container.

An example of the switching valve includes a rotary valve. The rotary valve may have a port to be connected to the syringe at the center of rotation. In this case, the syringe may be placed on the rotary valve.

The reaction container can be used for carrying out at least any one of color reaction, enzymatic reaction, fluorescence reaction, chemiluminescence reaction, and bioluminescence reaction.

In a case where the reaction container plate according to the present invention is intended to be used for measuring a gene-containing sample, a sample previously subjected to gene amplification reaction may be introduced into the reaction container plate. Alternatively, a gene amplification reagent may be previously contained in the reaction container or the reaction container plate may be designed to allow a gene amplification reagent to be dispensed into the reaction container so that gene amplification reaction can be carried out in the reaction container of the reaction container plate.

Examples of the gene amplification reaction include PCR method and LAMP method. For example, as PCR method for amplifying DNA, a method is proposed for directly subjecting a sample such as blood to PCR reaction without pretreating the sample. More specifically, this method is a nucleic acid synthesis method for amplifying a target gene contained in a gene-containing sample by adding a gene-containing body contained in the gene-containing sample or the gene-containing sample itself to a gene amplification reaction liquid and then adjusting the pH of the obtained reaction mixture to 8.5 to 9.5 (25° C.) (see Japanese Patent No. 3452717).

The reaction container may be made of an optically-transparent material so that optical measurement can be carried out from the bottom of the reaction container or from above the reaction container.

In a case where a liquid to be introduced into the reaction container channel contains a gene, the reaction container may contain a probe which reacts with the gene.

Further, the probe may be fluorescently-labeled.

The present invention is also directed to a reaction processing apparatus for processing the reaction container plate according to the present invention, including a syringe driving unit for driving the syringe and a switching valve driving unit for operating the switching valve.

EFFECT OF THE INVENTION

As described above, the reaction container plate according to the present invention includes a sealed reaction container, a reaction container channel connected to the reaction container, a sealed container provided separately from the reaction container, a sealed container channel connected to the sealed container, a syringe for sending a liquid, a switching valve for connecting the syringe to the reaction container channel or the sealed container channel, and a sealed container air vent channel of which one end is connected to the sealed container, and is processed using the reaction processing apparatus according to the present invention, and therefore, it is possible to prevent the entry of foreign matter from the outside of the reaction container plate and the pollution of an environment outside the reaction container plate with the liquid.

Further, since the reaction container plate includes the sealed container air vent channel communicating with the sealed container, it is possible to move a gas between the sealed container and the sealed container air vent channel when a liquid is injected into and sucked from the sealed container, thereby making it possible to smoothly inject and suck a liquid into and from the sealed container. Therefore, it is possible to prevent a phenomenon in which a liquid cannot be injected into and sucked from the sealed container due to an increase or decrease in the pressure in the sealed container.

In a case where the reaction container plate according to the present invention is intended to be used for measuring a gene-containing sample, the sample injected into the reaction container plate and then introduced into the reaction container can be processed in a closed system, and therefore, it is possible to prevent the pollution of an environment outside the reaction container plate and the pollution of the sample with foreign matter from outside the reaction container plate.

In the reaction container plate according to the present invention, a part of the sealed container air vent channel may be constituted from a narrow hole for maintaining the liquid-tightness of the sealed container in a state where there is no difference between the pressure in the sealed container and the pressure in the sealed container air vent channel. This makes it possible to prevent the leakage of a liquid to the outside through the sealed container air vent channel.

Further, the other end of the sealed container air vent channel may be hermetically sealed by being connected to a variable capacity part of which internal capacity is passively variable. This makes it possible to smoothly inject and suck a liquid into and from the sealed container because the internal capacity of the variable capacity part varies when the liquid is injected into and sucked from the sealed container. In addition, since the other end of the sealed container air vent channel is hermetically sealed, it is also possible to prevent the entry of foreign matter into the sealed container air vent channel from the outside and the leakage of the liquid to the outside.

As one configuration example of the reaction container and the reaction container channel, the reaction container plate further including a container base constituted from a substrate and having the reaction container of which opening is provided in a surface of the substrate, a channel base provided on the surface of the container base so as to cover the reaction container to seal the reaction container and having a top surface, a back surface, and an introduction hole extending from the top surface to the back surface and located above the reaction container, and a channel cover provided on the channel base and having a hollow space in a surface thereof opposed to the channel base so that an introduction channel passing above the introduction hole is formed from the hollow space and the top surface of the channel base can be mentioned. In this case, the reaction container channel is constituted from the introduction channel and the introduction hole, the introduction channel can be hermetically sealed, the introduction hole does not allow the passage of a liquid at an introduction pressure applied to the inside of the introduction channel to introduce the liquid into the introduction channel but allows the passage of the liquid at an injection pressure much higher than the introduction pressure applied to the inside of the introduction channel to inject the liquid contained in the introduction channel into the reaction container, and the channel cover has a flexible portion in at least a part thereof corresponding to a part of the introduction channel so that after the liquid is introduced into the introduction channel, the flexible portion of the channel cover is biased toward the channel base to apply the injection pressure to the inside of the introduction channel to inject the liquid into the reaction container through the introduction hole.

Therefore, the liquid can be injected into the reaction container while the reaction container is sealed to prevent the entry of foreign matter from the outside of the reaction container plate and the pollution of an environment outside the reaction container plate with the liquid.

In such a configuration example, at least the introduction hole and a portion around the introduction hole in the channel base may be constituted from an elastic member so that the introduction hole is elastically closed to such a degree that it does not allow the passage of the liquid at the introduction pressure applied to the inside of the introduction channel but is elastically opened to such a degree that it allows the passage of the liquid at the injection pressure applied to the inside of the introduction channel. This makes it possible to reliably inject the liquid contained in the introduction channel into the reaction container at the injection pressure applied to the inside of the introduction channel.

As described above, since the introduction hole provided in the reaction container plate according to the present invention does not allow the passage of a liquid at the introduction pressure applied to the inside of the introduction channel but allows the passage of the liquid at the injection pressure much higher than the introduction pressure applied to the inside of the introduction channel to inject the liquid contained in the introduction channel into the reaction container, the introduction hole needs to have a small inner diameter. However, when the introduction hole has a uniform inner diameter, it is necessary to apply a very high pressure to dispense a liquid contained in the introduction channel into the reaction container. Particularly, it is necessary to apply a high pressure when the contact angle of the channel base with a liquid is large (e.g., 90° or larger).

Therefore, a part of the introduction hole may have an inner diameter smaller than that of the introduction hole at the top surface of the channel base. This makes it possible to increase the inner diameter of the connecting hole at the top surface of the channel base opposed to the channel cover, thereby making it possible to dispense a liquid into the reaction container at a lower injection pressure as compared to a case where the introduction hole has a uniform inner diameter.

The container base may have a plurality of the reaction containers. In this case, by providing the introduction hole above each of the reaction containers and allowing the introduction channel to pass above the plurality of introduction holes, it is possible to inject a liquid into the plurality of reaction containers at the same time.

The channel base may have a projecting portion which projects from a surface thereof opposed to the reaction container plate into the reaction container. In this case, by allowing the projecting portion to have a proximal end and a distal end narrower than the proximal end and allowing the introduction hole to pass through the projecting portion, a liquid to be injected into the reaction container through the introduction hole can be easily dropped into the reaction container.

As another configuration example of the reaction container and the reaction container channel, a reaction container plate including a reaction container, a reaction container channel connected to the reaction container, and a reaction container air vent channel connected to the reaction container can be mentioned. In this case, the reaction container channel is constituted from a groove formed in the contact surface between two members bonded together or from the groove and a through hole formed in the member, and includes a main channel, a metering channel branched off the main channel and having a predetermined capacity, and an injection channel of which one end is connected to the metering channel and another end is connected to the reaction container, the main channel and the reaction container air vent channel can be hermetically sealed, and the injection channel is formed narrower than the metering channel, and does not allow the passage of a liquid at an introduction pressure applied to introduce the liquid into the main channel and the metering channel and at a purge pressure applied to purge the liquid from the main channel but allows the passage of the liquid at a pressure higher than the introduction pressure and the purge pressure.

Therefore, a liquid can be injected into the reaction container while the reaction container is sealed to prevent the entry of foreign matter from the outside of the reaction container plate and the pollution of an environment outside the reaction container plate with the liquid.

Further, since the reaction container plate includes the reaction container air vent channel connected to the reaction container, it is possible to move a gas between the reaction container and the reaction container air vent channel when a liquid is injected into the reaction container through the injection channel, thereby making it possible to smoothly inject a liquid into the reaction container. The reaction container air vent channel can be used to suck a gas contained in the reaction container to decompress the reaction container to inject a liquid into the reaction container.

In such a configuration example, the contact angle of the metering channel and the injection channel with a water droplet is preferably 90° or larger, and the area of an interface between the injection channel and the metering channel is preferably in a range of 1 to 10,000.000 $\mu m^2$. This makes it difficult for a liquid to enter the injection channel when the liquid is introduced into the main channel and the metering channel, thereby making it possible to increase an introduction pressure applied to introduce the liquid into the main channel and the metering channel.

The reaction container plate may include a plurality of the reaction containers. In this case, by providing the metering channel and the injection channel for each of the reaction containers and connecting a plurality of the metering channels to the main channel, it is possible to introduce a liquid into the plurality of metering channels one after another and then simultaneously inject the liquid into the plurality of reaction containers through the injection channels.

A projecting portion may be provided so as to project from a top inner surface of the reaction container. In this case, the other end of the injection channel is located at the tip of the projecting portion. By allowing the projecting portion to have a proximal end and a distal end narrower than the proximal end, a liquid to be injected into the reaction container through the injection channel can be easily dropped into the reaction container.

The reaction container plate according to the present invention may include a sample container for containing a sample liquid as the sealed container. In this case, it is possible to eliminate the necessity to separately prepare a container for containing a sample.

The sample container may be hermetically sealed with an elastic member which allows a dispensing device having a sharp tip to pass through to form a through hole and which also allows the through hole to be closed by pulling out the dispensing device due to its elasticity. This makes it possible to inject a sample liquid into the sample container sealed with the elastic member and then to prevent the sample liquid from leaking out of the sample container.

Further, the sample container may previously contain a liquid for pretreating a sample or a reagent. This makes it possible to eliminate the necessity to dispense a liquid for pretreating a sample or a reagent into the sample container.

The reaction container plate according to the present invention may further include one or more reagent containers, each of which is constituted from the sealed container, other than the sample container. By allowing the reagent container to previously contain a reagent to be used for the reaction of a sample liquid and sealing it with a film, or by allowing the reagent container to have an openable and closable cap so that the reagent can be injected thereinto, it is possible to eliminate the necessity to separately prepare a container for containing the reagent.

The reaction container plate according to the present invention may further include a gene amplification container which is constituted from the sealed container and used for carrying out gene amplification reaction. By providing such a gene amplification container, it is possible to amplify a target gene in the reaction container plate by gene amplification reaction such as PCR method or LAMP method even when a sample liquid contains only a very small amount of the target gene, thereby increasing analytical precision.

The switching valve may be a rotary valve. In this case, by providing a port to be connected to the syringe at the center of rotation of the rotary valve, it is possible to simplify a channel configuration.

Further, by providing a port to be connected to the syringe at the center of rotation of the rotary valve and placing the syringe on the rotary valve, it is possible to shorten or eliminate a channel between the port and the syringe, thereby simplifying the structure of the reaction container plate. In addition, it is also possible to effectively utilize a region on the switching valve, thereby making it possible to make the planar size of the reaction container plate smaller as compared to a case where the syringe is placed in a region other than the region on the switching valve.

The reaction container plate may be intended to be used for measuring a gene-containing sample. In this case, by allowing the reaction container to be used for carrying out gene amplification reaction, it is possible to eliminate the necessity to prepare a sample previously subjected to gene amplification reaction.

A sample injected into the reaction container plate and then introduced into the reaction container can be processed in a closed system, and therefore, it is possible to prevent the pollution of an environment outside the reaction container plate and the contamination of the sample with foreign matter coming from the outside of the reaction container plate.

Further, the reaction container may be made of an optically-transparent material so that optical measurement can be carried out from the bottom of the reaction container or from above the reaction container. This makes it possible to optically measure a liquid contained in the reaction container without transferring the liquid into another container.

In a case where a liquid to be introduced into the reaction container channel contains a gene, the reaction container may contain a probe which reacts with the gene. This makes it possible to detect a gene having a base sequence corresponding to the probe in the reaction container.

Figure 1A:
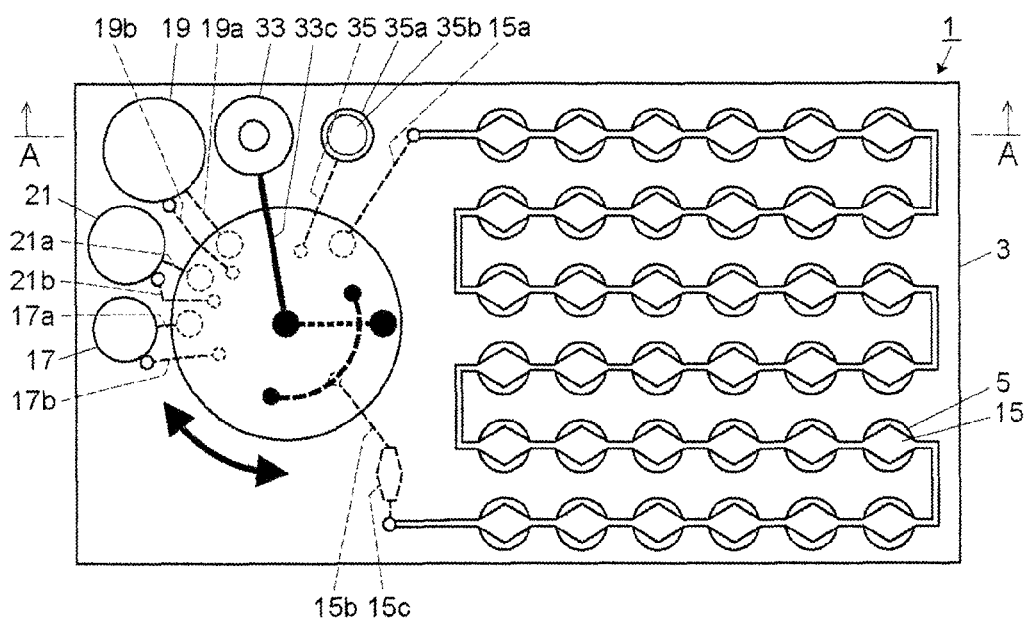
FIG. 1A is a plan view of one embodiment of a reaction container plate according to the present invention.

DESCRIPTION OF REFERENCE NUMERALS 1 reaction container plate
3 container base
5 reaction container
11 channel base
11a projecting portion
11b introduction hole
12 introduction hole
12a channel
12b channel
13 channel cover
15 introduction channel
17 sample container
17b, 17d, 17e air vent channel
19 reagent container
19b, 19d, 19e air vent channel
21 reagent container
21b, 21d air vent channel
33 syringe
35 air vent channel
35b bellows
47 switching valve
59 channel base
60 introduction hole
60a channel
60b channel
101 reaction container plate
103 container base 105 reaction container
111 channel base
113 main channel
115 metering channel
117 injection channel
119, 121 reaction container air vent channel
135 sample container
135b, 135d, 135e sample container air vent channel
137 reagent container
137b, 137d, 137e reagent container air vent channel
139 container for air suction
139b, 139d, 139e air vent channel for container for air suction
151 syringe
163 switching valve
173 channel spacer
175 projecting portion
177 injection channel
179 reaction container air vent channel

BEST MODE FOR CARRYING OUT THE INVENTION

Figure 1B:
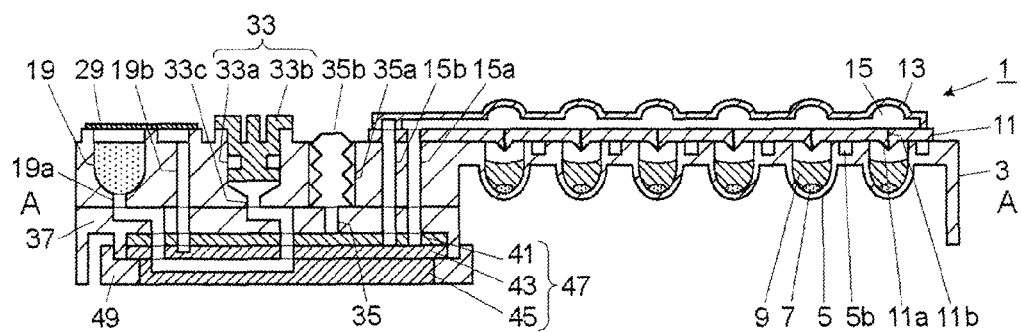
FIG. 1B is a sectional view taken along the A-A line in FIG. 1A, which further includes a sectional view of a switching valve.
Figure 2:
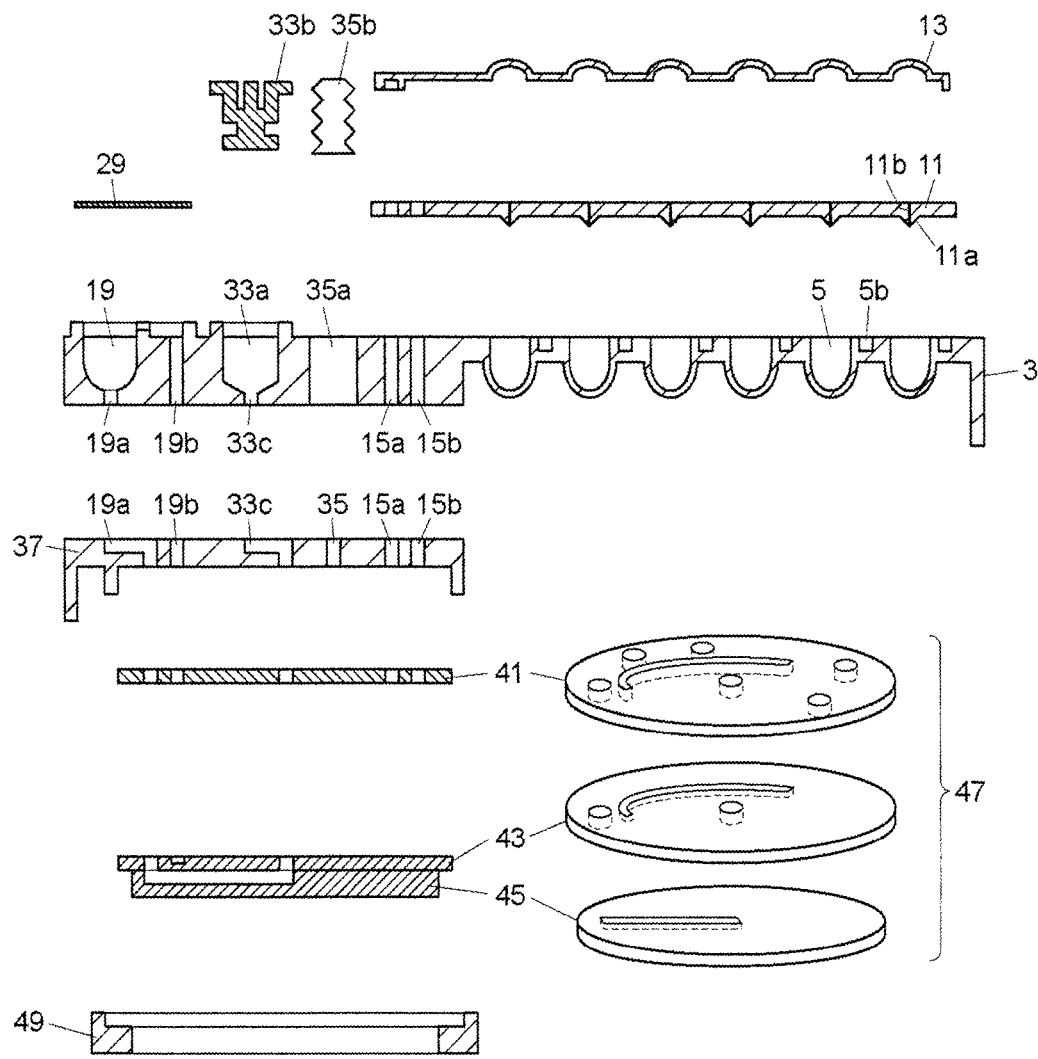
FIG. 2 shows an exploded sectional view of the reaction container plate in the embodiment and an exploded perspective view of the switching valve.
Figure 3:
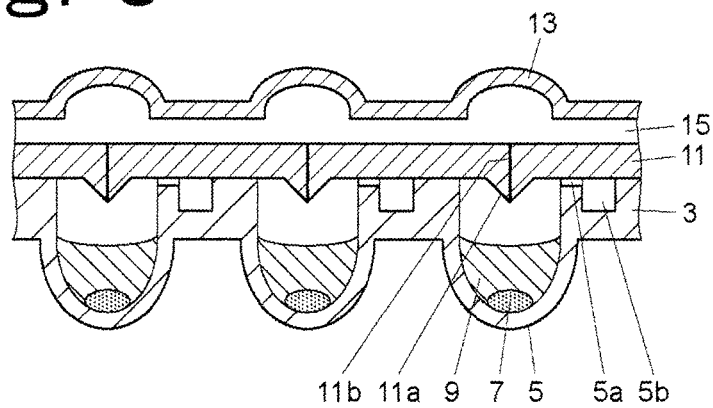
FIG. 3 is an expanded sectional view of reaction containers of the reaction container plate in the embodiment.
Figure 4A:
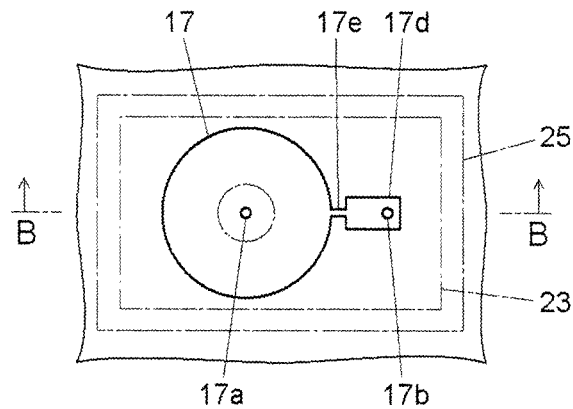
FIG. 4A is an expanded plan view of a sample container of the reaction container plate in the embodiment.
Figure 4B:
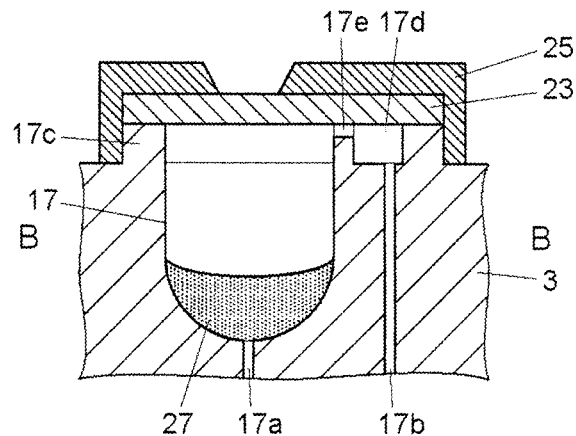
FIG. 4B is a sectional view taken along the B-B line in FIG. 4A.
Figure 5A:
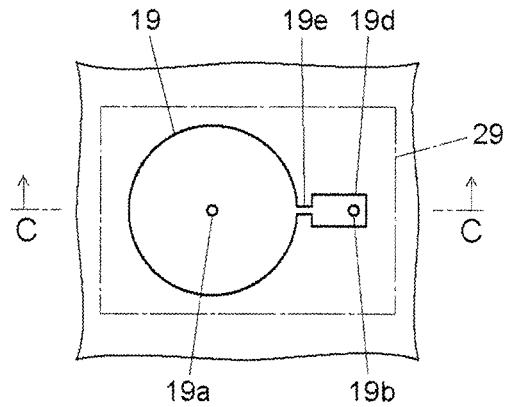
FIG. 5A is an expanded plan view of a reagent container of the reaction container plate in the embodiment.
Figure 5B:
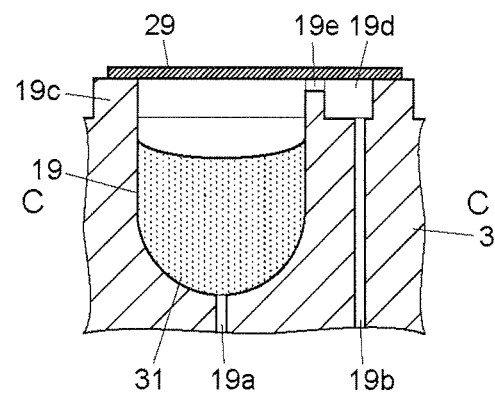
FIG. 5B is a sectional view taken along the C-C line in FIG. 5A.

FIG. 1A is a plan view of one embodiment of a reaction container plate according to the present invention, and FIG. 1B is a sectional view taken along the A-A line in FIG. 1A, which further includes a sectional view of a switching valve. FIG. 2 shows an exploded sectional view of the reaction container plate in the embodiment shown in FIG. 1A and an exploded perspective view of the switching valve. FIG. 3 is an expanded sectional view of reaction containers of the reaction container plate in the embodiment shown in FIG. 1A. FIG. 4A is an expanded plan view of a sample container, and FIG. 4B is a sectional view taken along the B-B line in FIG. 4A. FIG. 5A is an expanded plan view of a reagent container, and FIG. 5B is a sectional view taken along the C-C line in FIG. 5A.

With reference to FIGS. 1A to 5B, the reaction container plate according to one embodiment of the present invention will be described.

A reaction container plate 1 includes a plurality of reaction containers 5 each having an opening in one surface of a container base 3. In the reaction container plate 1 according to this embodiment of the present invention, the reaction containers 5 are arranged in a matrix of 6 rows and 6 columns, and each of the reaction containers 5 contains a reagent 7 and a wax 9.

The material of the container base 3 including the reaction containers 5 is not particularly limited. However, in a case where the reaction container plate 1 is intended to be disposable, the material of the container base 3 is preferably a cheaply-available material. Preferred examples of such a material include resin materials such as polypropylene and polycarbonate. In a case where the reaction container plate 1 is intended to be used for performing detection by absorbance, fluorescence, chemiluminescence, or bioluminescence in the reaction container 5 or a detection portion separately provided, the container base 3 is preferably made of an optically-transparent resin so that optical detection can be carried out from the bottom of the reaction container 5. Particularly, in a case where the reaction container plate 1 is intended to be used for fluorescence detection, the container base 3 is preferably made of a low self-fluorescent (i.e., fluorescence emitted from a material itself is weak) and optically-transparent resin such as polycarbonate. The thickness of the container base 3 is in a range of 0.2 to 4.0 mm, preferably in a range of 1.0 to 2.0 mm. From the viewpoint of low self-fluorescence, the thickness of the container base 3 for fluorescence detection is preferably small.

Referring to FIGS. 1A, 1B and 3, a channel base 11 (not shown in FIG. 1A) is provided on the container base 3 so as to cover a region where the reaction containers 5 are arranged. The channel base 11 is made of an elastic material such as silicone rubber or PDMS (polydimethylsiloxane). The thickness of the channel base 11 is, for example, 1.0 mm. The channel base 11 has a projecting portion 11a which projects from the surface thereof opposed to the container base 3 into each of the reaction containers 5. The projecting portion 11a is substantially trapezoidal in cross section. For example, the proximal end of the projecting portion 11a has a width of 1.0 to 2.8 mm, and the distal end of the projecting portion 11a has a width of 0.2 to 0.5 mm. That is, the distal end of the projecting portion 11a is narrower than the proximal end of the projecting portion 11a.

In the channel base 11, an introduction hole 11b is provided at a position where each of the projecting portions 11a is provided so as to extend from the distal end of the projecting portion 11a to the surface of the channel base 11 where the projecting portion 11a is not provided. The introduction hole 11b is closed to such a degree that it does not allow the passage of a liquid due to the elasticity of the material of the channel base 11.

On the channel base 11, a channel cover 13 (not shown in FIG. 1A) is provided. The channel cover 13 has a thickness of, for example, 0.2 to 0.5 mm and is made of, for example, a flexible material such as silicone rubber or PDMS. One surface of the channel cover 13 opposed to the channel base 11 has a recess, and the recess and the surface of the channel base 11 constitute an introduction channel 15. The introduction channel 15 is formed so as to pass above all the 36 introduction holes 11b. In the introduction channel 15, portions located above the reaction containers 5 have a larger width than other portions.

As shown in FIG. 3, an air vent channel 5a communicating with the reaction container 5 is provided for each of the reaction containers 5 in the surface of the container base 3 in a region where the reaction containers 5 are arranged. Further, a plurality of air vent channels 5b each constituted from a groove communicating with the plurality of air vent channels 5a are provided. Each of the air vent channels 5b extends in a direction perpendicular to the plane of the paper. The plurality of air vent channels 5b communicate with each other in a region not shown. The air vent channels 5a and the air vent channels 5b are covered with the channel base 11. Each of the air vent channels 5a is formed so as to have a width of, for example, 5 to 500 μm and a depth of, for example, 5 to 500 μm.

Referring to FIGS. 1A, 1B, 4A, and 4B, a sample container 17 and reagent containers 19 and 21 are provided in the surface of the container base 3 at positions other than the position of a region where the reaction containers 5 are arranged. The sample container 17 and the reagent containers 19 and 21 constitute sealed containers of the reaction container plate according to the present invention.

In the container base 3, a sample channel 17a extending from the bottom of the sample container 17 to the back surface of the container base 3 and a sample air vent channel 17b extending from the top surface to the back surface of the container base 3 are provided in the vicinity of the sample container 17. On the container base 3, a projecting portion 17c is provided so as to surround an opening of the sample container 17. In the projecting portion 17c, a sample air vent channel 17d constituted from a through hole is provided so as to be located above the sample air vent channel 17b. In the surface of the projecting portion 17c, a sample air vent channel 17e which allows the sample container 17 to communicate with the sample air vent channel 17d is provided.

The sample air vent channel 17e is constituted from one or more narrow holes, and each narrow hole has a width of, for example, 5 to 200 μm and a depth of, for example, 5 to 200 μm. The sample air vent channel 17e is provided to maintain the liquid-tightness of the sample container 17 in a state where there is no difference between the pressure in the sample container 17 and the pressure in the sample air vent channel 17d. On the projecting portion 17c, a septum 23 as an elastic member to cover the sample container 17 and the sample air vent channel 17d is provided. The septum 23 is made of, for example, an elastic material such as silicone rubber or PDMS. Therefore, a dispensing device having a sharp tip can pass through the septum 23 to form a through hole, but the through hole can be closed by pulling out the dispensing device out of the septum 23 due to its elasticity. On the septum 23, a septum stopper 25 for fixing the septum 23 is provided. The septum stopper 25 has an opening located above the sample container 17. According to the present embodiment, a reagent 27 is previously contained in the sample container 17.

In the container base 3, a reagent channel 19a extending from the bottom of the reagent container 19 to the back surface of the container base 3 and a reagent air vent channel 19b extending from the top surface to the back surface of the container base 3 are provided in the vicinity of the reagent container 19. On the container base 3, a projecting portion 19c is provided so as to surround an opening of the reagent container 19. In the projecting portion 19c, a reagent air vent channel 19d constituted from a through hole is provided so as to be located above the reagent air vent channel 19b. In the surface of the projecting portion 19c, a reagent air vent channel 19e which allows the reagent container 19 to communicate with the reagent air vent channel 19d is provided.

The reagent air vent channel 19e is constituted from one or more narrow holes, and each narrow hole has a width of, for example, 5 to 200 μm and a depth of, for example, 5 to 200 μm. The reagent air vent channel 19e is provided to maintain the liquid-tightness of the reagent container 19 in a state where there is no difference between the pressure in the reagent container 19 and the pressure in the reagent air vent channel 19d. On the projecting portion 19c, a film 29 made of, for example, aluminum to cover the reagent container 19 and the reagent air vent channel 19d is provided. In the reagent container 19, a reagent 31 is contained.

Although a detailed structure of the reagent container 21 is not shown, the reagent container 21 has the same structure as the reagent container 19. That is, in the container base 3, a reagent container channel 21a extending from the bottom of the reagent container 21 to the back surface of the container base 3 and a reagent container air vent channel 21b extending from the top surface to the back surface of the container base 3 are provided in the vicinity of the reagent container 21. On the container base 3, a spacer having air vent channels is provided so as to surround an opening of the reagent container 21. On the projecting portion, a film made of, for example, aluminum is provided.

Referring to FIGS. 1A, 1B, and 2, in the surface of the container base 3, a syringe 33 is provided at a position other than the positions of a region where the reaction containers 5 are arranged, and the containers 17, 19, and 21. The syringe 33 is constituted from a cylinder 33a formed in the container base 3 and a plunger 33b placed in the cylinder 33a. In the container base 3, a syringe channel 33c extending from the bottom of the cylinder 33a to the back surface of the container base 3 is provided.

In the container base 3, a bellows 35b (variable capacity part) is also provided at a position other than the positions of a region where the reaction containers 5 are arranged, the containers 17, 19 and 21, and the syringe 33. The bellows 35b expands and contracts, and therefore, the internal capacity of the bellows 35b is passively variable. The bellows 35b is placed in, for example, a through hole 35a provided in the container base 3.

In the container base 3, an introduction channel 15a and a drain channel 15b are also provided. The introduction channel 15a and the drain channel 15b each extend from the top surface to the back surface of the container base 3. The introduction channel 15a is connected to one end of the introduction channel 15 provided between the channel base 11 and the channel cover 13 through a through hole provided in the channel base 11. The drain channel 15b is connected to the other end of the introduction channel 15 through another through hole provided in the channel base 11. In the drain channel 15b, a drain space 15c is provided. The air vent channels 5b described above with reference to FIG. 3 are connected to the drain space 15c.

A container bottom 37 is attached to the back surface of the container base 3 at a position other than the position of a region where the reaction containers 5 are arranged. In the container bottom 37, an air vent channel 35 is provided at a position allowing the air vent channel 35 to communicate with the bellows 35b. The bellows 35b is connected to the container bottom 37 so as to be in close contact with the surface of the container bottom 37. The container bottom 37 is provided to guide the channels 15a, 15b, 17a, 17b, 19a, 19b, 21a, 21b, 33c, and 35 to predetermined port positions.

On the surface of the container bottom 37 located on the opposite side from the container base 3, a rotary switching valve 47 is provided. The rotary switching valve 47 is constituted from disk-shaped sealing plate 41, rotor upper 43, and rotor base 45. The switching valve 47 is attached to the container bottom 37 by means of a lock 49.

The sealing plate 41 has four through holes provided for the channels 15a, 17a, 19a, and 21a, respectively, a through groove provided for the channels 15b, 17b, 19b, 21b, and 35, and a through hole provided at the center thereof so as to communicate with the syringe channel 33c. The four through holes are provided in the vicinity of the peripheral portion of the sealing plate 41 and on a circle concentric with the sealing plate 41. The through groove is provided inside the four through holes and on a circle concentric with the sealing plate 41.

The rotor upper 43 has a through hole connected to any one of the channels 15a, 17a, 19a, and 21a, a groove provided in the surface thereof so as to correspond to the through groove provided in the sealing plate 41, and a through hole provided at the center thereof so as to communicate with the syringe channel 33c.

The rotor base 45 has a groove provided in the surface thereof to connect the through hole provided at the center of the rotor upper 43 and the through hole provided in the peripheral portion of the rotor upper 43 to each other.

By rotating the switching valve 47, the syringe channel 33c is connected to any one of the channels 15a, 17a, 19a, and 21a, and at the same time, the air vent channel 35 is connected to any one or more of the channels 15b, 17b, 19b, 21b, and 35.

The switching valve 47 shown in FIG. 1A indicate its initial state where the syringe channel 33c is not connected to any one of the channels 15a, 17a, 19a, and 21a, and the air vent channel 35 is not connected to any one of the channels 15b, 17b, 19b, 21b, and 35, either. At this time, since the channels 15a and 15b are not connected to any ports, the introduction channel 15 is hermetically sealed.

Figure 6:
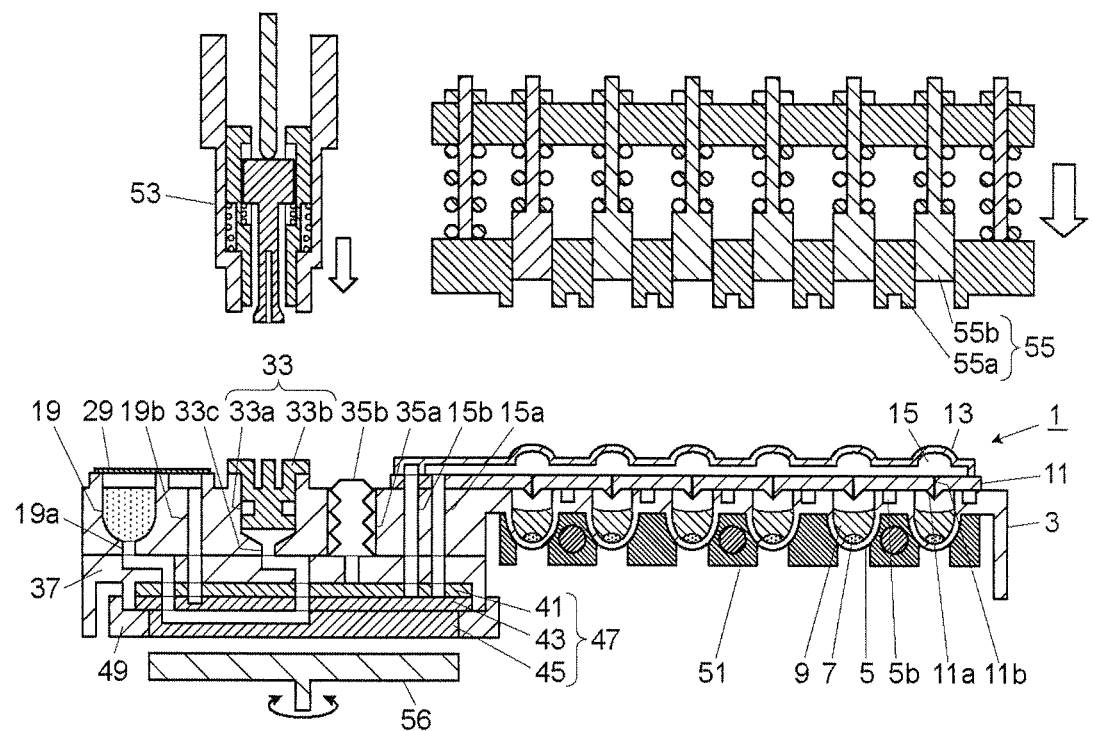
FIG. 6 is a sectional view showing the reaction container plate in the embodiment and one embodiment of a reaction processing apparatus according to the present invention.

FIG. 6 is a sectional view showing the reaction container plate 1 shown in FIG. 1 and a reaction processing apparatus for processing the reaction container plate 1. The reaction container plate 1 shown in FIG. 6 has the same structure as that shown in FIG. 1, and therefore the description thereof is not given.

The reaction processing apparatus includes a temperature control system 51 for controlling the temperature of the reaction containers 5, a syringe driving unit 53 for driving the syringe 33, and a biasing system 55 for biasing the channel cover 13 toward the channel base 11. The biasing system 55 has a first unit 55a for pressing the channel cover 13 at positions corresponding to the positions of areas around the reaction containers 5 and a second unit 55b for pressing the channel cover 13 at positions corresponding to the positions of the reaction containers 5. The reaction processing apparatus further includes a switching valve driving unit 56 for switching the switching valve 47.

Figure 7:
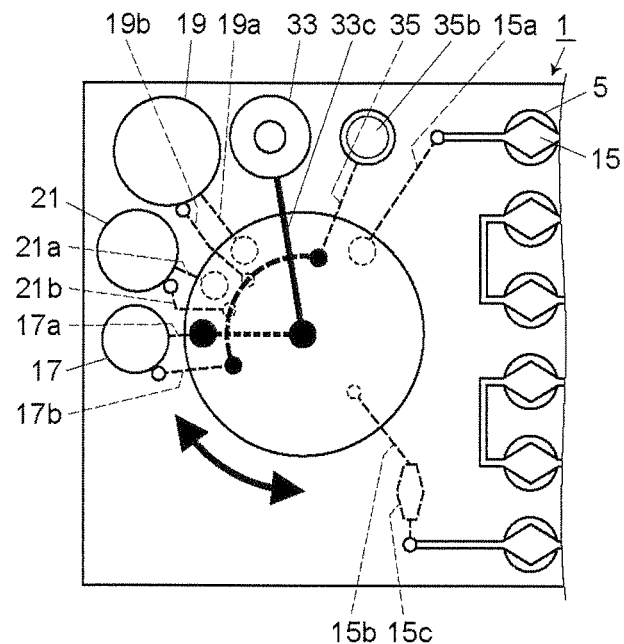
FIG. 7 is a plan view showing the connection state of the switching valve for explaining the operation of introducing a sample liquid into an introduction channel from the sample container.
Figure 8:
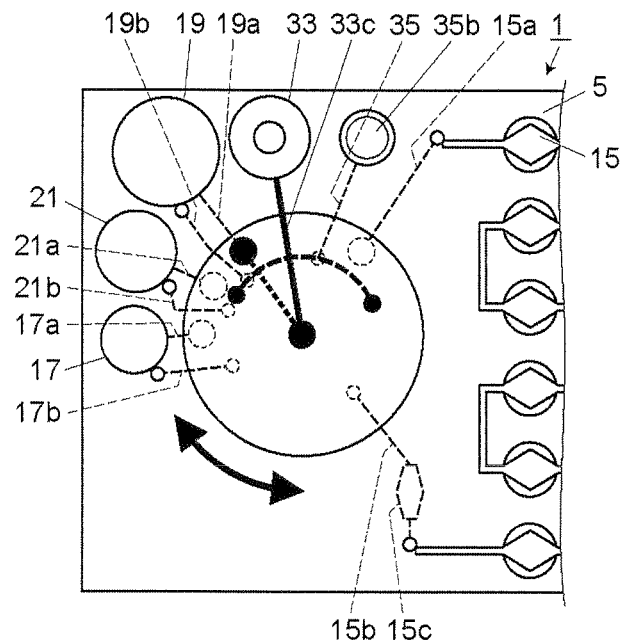
FIG. 8 is a plan view showing the connection state of the switching valve for explaining operation following the operation explained with reference to FIG. 7.
Figure 9:
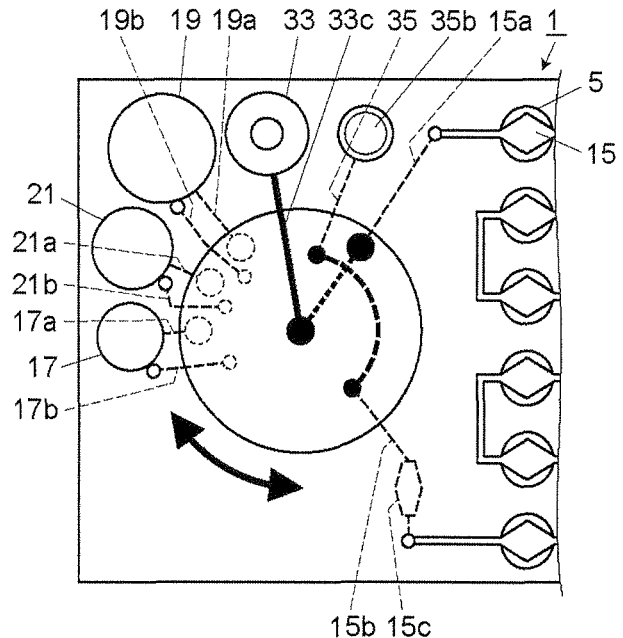
FIG. 9 is a plan view showing the connection state of the switching valve for explaining operation following the operation explained with reference to FIG. 8.

FIGS. 7 to 9 are plan views showing the connection state of the switching valve 47 for explaining the operation of introducing a sample liquid into the introduction channel 15 from the sample container 17. This operation will be described with reference to FIGS. 1 and 6 to 9.

The syringe driving unit 53 is connected to the syringe 33, and the switching valve driving unit 56 is connected to the switching valve 47.

As shown in FIG. 7, the switching valve 47 in its initial state shown in FIG. 1A is rotated to connect the sample channel 17a to the syringe channel 33c and to connect the air vent channel 17b to the air vent channel 35. At this time, the air vent channels 19b and 21b are also connected to the air vent channel 35.

A dispensing device having a sharp tip (not shown) is prepared, and the dispending device is passed through the septum 23 provided on the sample container 17 to dispense a sample liquid into the sample container 17. At this time, a gas contained in the sample container 17 is discharged into the air vent channel 17e due to the entry of the dispensing device into the sample container 17 and the dispensing of the sample liquid into the sample container 17. After the completion of the dispensing of the sample liquid, the dispensing device is pulled out of the septum 23. At this time, a gas flows into the sample container 17 through the air vent channel 17e due to the removal of the dispensing device from the sample container 17. By pulling the dispensing device out of the septum 23, a through hole formed in the septum 23 is closed due to the elasticity of the septum 23. In a case where the volume of a gas contained in the sample container 17 greatly varies, the bellows 35b connected to the sample container 17 through the air vent channels 17e, 17d, and 17b, the switching valve 47, and the air vent channel 35 expands and contracts.

The syringe 33 is slidably moved to mix the sample liquid and the reagent 27 contained in the sample container 17. Then, the thus obtained liquid mixture contained in the sample container 17 is sucked into the channel in the switching valve 47, the syringe channel 33c, and the syringe 33. At this time, the bellows 35b expands and contracts with changes in the volume of a gas contained in the sample container 17 because the sample container 17 is connected to the bellows 35b through the air vent channels 17e, 17d, and 17b, the switching valve 47, and the air vent channel 35.

As shown in FIG. 8, the switching valve 47 is rotated to connect the reagent channel 19a to the syringe channel 33c and to connect the air vent channel 19b to the air vent channel 35. The liquid mixture sucked into the channel in the switching valve 47, the syringe channel 33c, and the syringe 33 is dispensed into the reagent container 19 and is further mixed with the reagent 31. The obtained liquid mixture is sucked into the channel in the switching valve 47, the syringe channel 33c, and the syringe 33. At this time, the bellows 35b expands and contracts with changes in the volume of a gas contained in the reagent container 19 because the reagent container 19 is connected to the bellows 35b through the air vent channels 19e, 19d, and 19b, the switching valve 47, and the air vent channel 35. It is to be noted that the reagent container 21 is not used in the operation described here.

As shown in FIG. 9, the switching valve 47 is rotated to connect the introduction channel 15a to the syringe channel 33c and to connect the drain channel 15b to the air vent channel 35. This allows the syringe 33, the introduction channels 15a and 15, the drain channel 15b, and the air vent channel 3, and the bellows 35b to communicate with each other. The liquid mixture sucked into the channel in the switching valve 47, the syringe channel 33c, and the syringe 33 is dispensed into the introduction channel 15a and then into the introduction channel 15. The liquid mixture introduced into the drain channel 15b through the introduction channel 15 is stored in the drain space 15c. At this time, the bellows 35b expands.

Figure 10A:
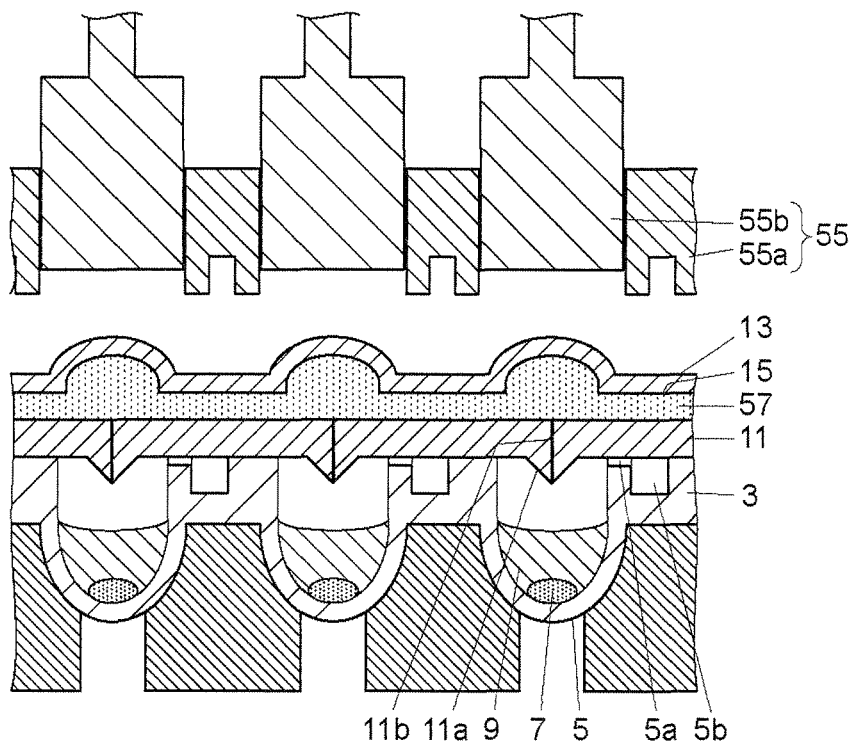
FIG. 10A is an expanded sectional view of reaction containers and their vicinity for explaining operation following the operation of introducing a liquid into the introduction channel 15, which shows a state in which the introduction channel 15 is filled with the liquid.
Figure 10B:
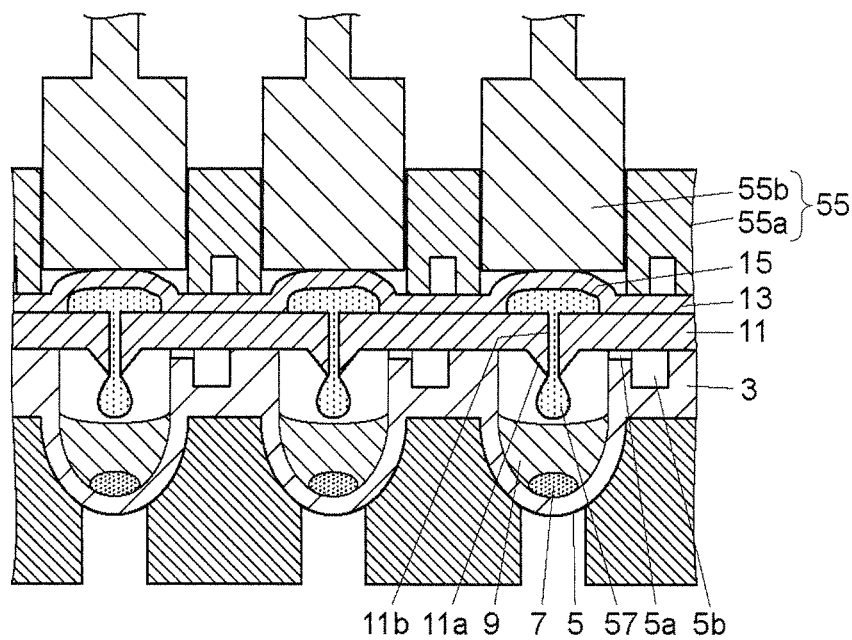
FIG. 10B is an expanded sectional view of reaction containers and their vicinity for explaining operation following the operation of introducing a liquid into the introduction channel 15, which shows a state in which the liquid is dispensed into the reaction containers.

FIGS. 10A and 10B are expanded sectional views of reaction containers and their vicinity for explaining operation following the operation of introducing a liquid into the introduction channel 15, wherein FIG. 10A shows a state in which the introduction channel 15 is filled with the liquid and FIG. 10B shows a state in which the liquid is dispensed into the reaction containers.

As shown in FIG. 10A, the introduction channel 15 is filled with a liquid mixture 57.

The switching valve 47 is kept in the connection state shown in FIG. 9, and as shown in FIG. 10B, the biasing system 55 is moved toward the reaction container plate 1 so that the first unit 55a located closer to the reaction container plate 1 than the second unit 55b presses the channel cover 13 against the channel base 11 at positions corresponding to the positions of areas around the reaction containers 5. This makes it possible to form sealed introduction channel spaces containing the liquid mixture 57 above the introduction holes 11b located above the reaction containers 5.

Then, the biasing system 55 is further moved toward the reaction container plate 1 so that the second unit 55b biases the channel cover 13 covering the sealed introduction channel spaces toward the channel base 11. This increases the pressure in the sealed introduction channel spaces so that the introduction holes 11b are elastically opened and the liquid mixture 57 is dispensed into the reaction containers 5. At this time, the reaction containers 5 are connected to the air vent channel 35 through the air vent channels 5a, the air layers 5b, and the drain space 15c, and therefore, a gas contained in the reaction containers 5 can be moved toward the air vent channels 5a. This makes it possible to reduce an increase in the pressure in the reaction containers 5, thereby facilitating the dispensing of the liquid mixture 57 into the reaction containers 5.

Then, the biasing system 55 is moved away from the reaction container plate 1 so that the pressure in the introduction channel 15 is reduced and the introduction holes 11b are elastically closed. Then, the switching valve 47 is returned to its initial state shown in FIG. 1B to hermetically seal the introduction channel 15 to prevent the leakage of the liquid mixture 57 and a liquid contained in the reaction containers 5 to the outside.

Then, the reaction containers 5 are heated by the temperature control system 51 to melt the wax 9 to react the liquid mixture 57 with the reagent 7. It is to be noted that the wax 9 may be melted by heating the reaction containers 5 by the temperature control system 51 before the dispensing of the liquid mixture 57 into the reaction containers 5 so that the liquid mixture 57 is dispensed into the reaction containers 5 containing the melted wax 9.

Figure 11A:
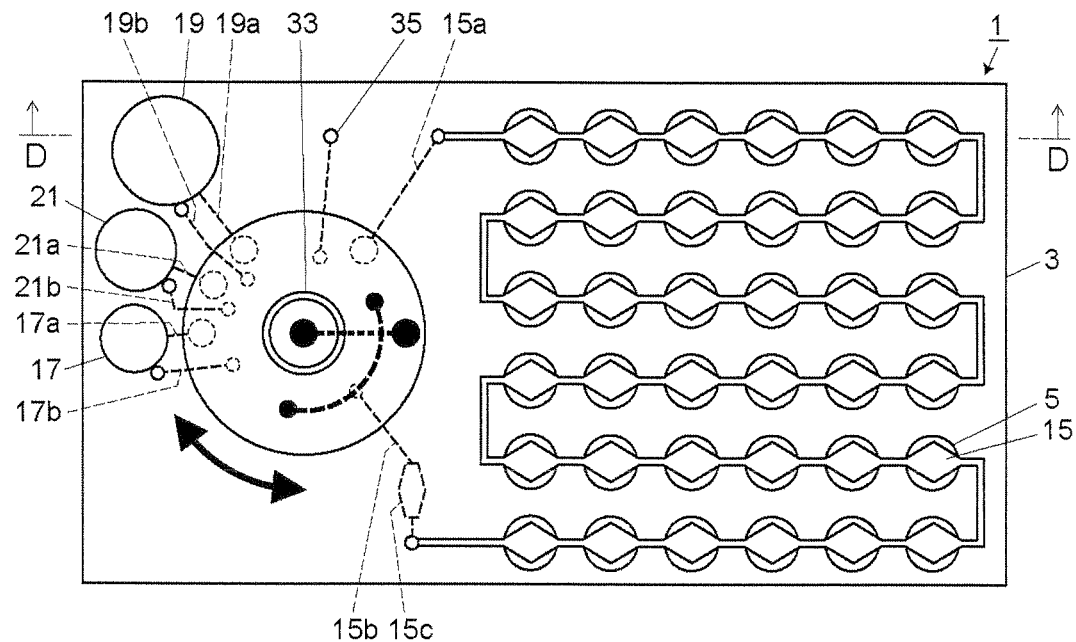
FIG. 11A is a plan view of a reaction container plate according to another embodiment of the present invention.
Figure 11B:
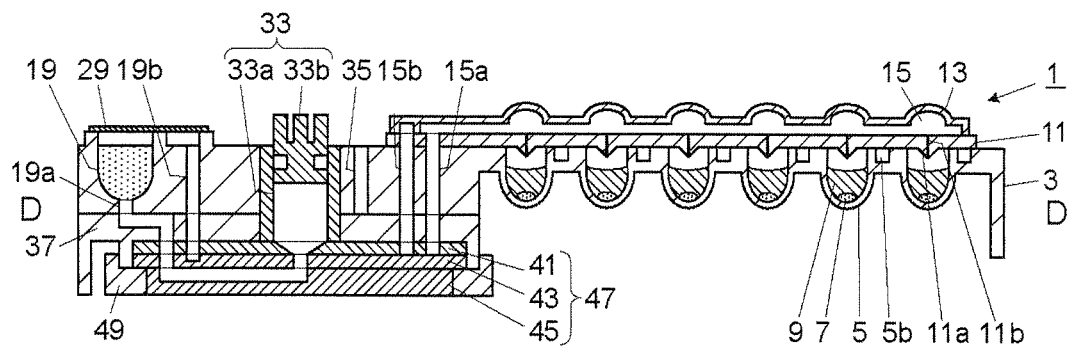
FIG. 11B is a sectional view taken along the D-D line in FIG. 11A.

FIG. 11A is a plan view of a reaction container plate according to another embodiment of the present invention, and FIG. 11B is a sectional view taken along the D-D line in FIG. 11A, which further includes a sectional view of a switching valve. It is to be noted that in FIG. 11, components performing the same functions as those shown in FIG. 1 are represented by the same reference numerals as in FIG. 1, and the description of such components will not be given.

The reaction container plate according to the embodiment of the present invention shown in FIG. 11 is different from the reaction container plate shown in FIG. 1 in that the syringe 33 is placed on the switching valve 47. This makes it possible to eliminate the necessity to provide a channel between the switching valve 47 and the syringe 33, thereby simplifying the structure of the reaction container plate. In addition, it is also possible to effectively utilize a region on the switching valve 47, thereby making it possible to make the planar size of the reaction container plate 1 smaller as compared to a case where the syringe 33 is placed in a region other than the region on the switching valve 47.

Further, the reaction container plate according to the embodiment of the present invention shown in FIG. 11 is different from the reaction container plate shown in FIG. 1 also in that the air vent channel 35 is not connected to a bellows. However, as in the case of the reaction container plate shown in FIG. 1, the reaction container plate shown in FIG. 11 may include the bellows 35b. It is to be noted that the reaction container plate 1 shown in FIG. 11 can prevent the leakage of a liquid to the outside even when the end of the air vent channel 35 is not sealed with a variable capacity part such as a bellows because the channels 15a, 15b, 17b, 19b, and 21b can be cut off from the outside by appropriately selecting the connection state of the switching valve 47.

Figure 12:
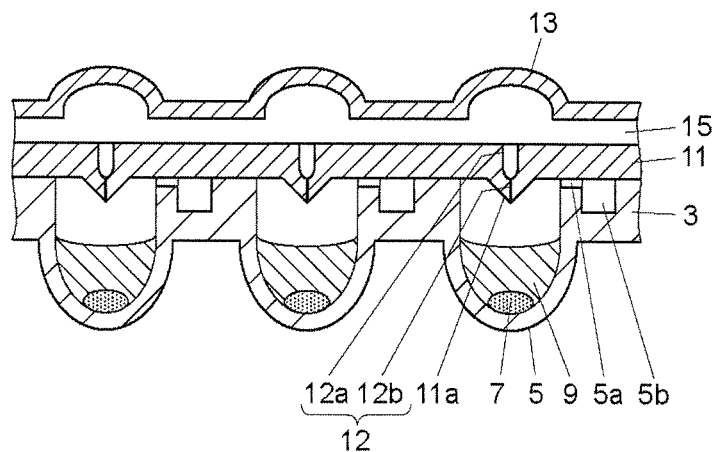
FIG. 12 is an expanded sectional view of reaction containers of a reaction container plate according to another embodiment of the present invention and their vicinity.

FIG. 12 is an expanded sectional view of reaction containers of a reaction container plate according to still another embodiment of the present invention and their vicinity. The reaction container plate according to the embodiment of the present invention shown in FIG. 12 is the same as the reaction container plate described above with reference to FIGS. 1 to 5 except for the structure of the introduction hole provided in the channel base.

An introduction hole 12 provided in the channel base 11 is constituted from a channel 12a provided in the surface of the channel base 11 opposed to the channel cover 13 and a channel 12b extending from the bottom of the channel 12a to the tip of the projecting portion 11a. The inner diameter of the channel 12b is smaller than that of the channel 12a at the surface of the channel base 11. The channel 12b is closed due to the elasticity of the material of the channel base 11 to such a degree that it does not allow the passage of a liquid. The inner diameter of the channel 12a at the surface of the channel base 11 is in a range of, for example, 100 µm to 2 mm.

Such a structure of the introduction hole 12 makes it possible to increase the inner diameter of the introduction hole 12 at the surface of the channel base 11 opposed to the channel cover 13, thereby making it possible to dispense a liquid into the reaction container 5 at a smaller injection pressure as compared to a case where the introduction hole has a uniform inner diameter.

When a liquid is dispensed into the reaction container 5, the channel 12b is elastically opened in the same manner as in the case shown in FIG. 10B to dispense the liquid into the reaction container 5.

Figure 13:
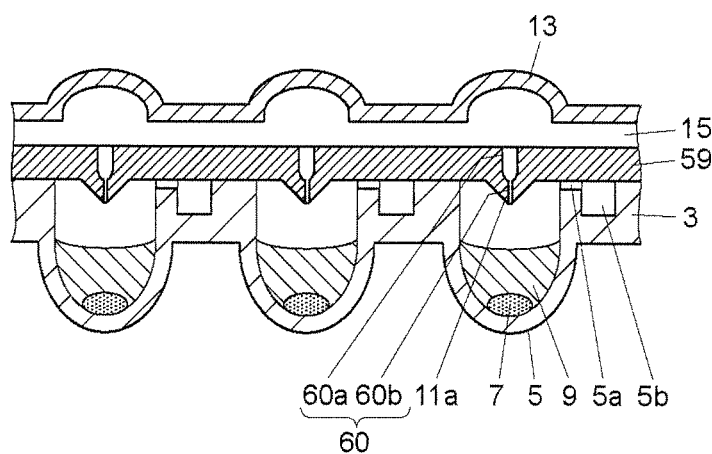
FIG. 13 is an expanded sectional view of reaction containers of a reaction container plate according to another embodiment of the present invention and their vicinity.

FIG. 13 is an expanded sectional view of reaction containers of a reaction container plate according to still another embodiment of the present invention and their vicinity. The reaction container plate according to the embodiment of the present invention shown in FIG. 13 is the same as the reaction container plate described above with reference to FIGS. 1 to 5 except for the material of the channel base and the structure of the introduction hole.

A channel base 59 is made of, for example, a hard material such as PMMA (acrylic resin), PC (polycarbonate), COC (cycloolefin copolymer), or COP (cycloolefin polymer) or an elastic material such as PDMS. In the channel base 59, an introduction hole 60 is provided at a position where each of the projecting portions 11a is provided so as to extend from the distal end of the projecting portion 11a to the surface of the channel base 59 where the projecting portion 11a is not provided. The introduction hole 60 is constituted from a channel 60a provided in the surface of the channel base 59 opposed to the channel cover 13 and a channel 60b extending from the bottom of the channel 60a to the tip of the projecting portion 11a. The inner diameter of the channel 60b is in a range of, for example, 1 µm to 2 mm, which is smaller than the inner diameter of the channel 60a at the surface of the channel base 11 (e.g., 100 µm to 3 mm).

The channel 60b is formed so as to have a size that does not allow the passage of a liquid at an introduction pressure applied to the inside of the introduction channel 15 to introduce the liquid into the introduction channel 15 but allows the passage of the liquid at an injection pressure much higher than the introduction pressure applied to the inside of the introduction channel 15 to inject the liquid contained in the introduction channel 15 into the reaction container 5. For example, in a case where a liquid to be introduced into the introduction channel 15 is hydrophilic, an inner wall of the channel 60b made of a hydrophobic material can effectively prevent the liquid from being introduced into the reaction container 5 through the channel 60b at the introduction pressure. However; the channel 60b is not limited to one having an inner wall made of a hydrophobic material. The channel base 59 may be made of an elastic material.

In the case of the reaction container plate according to the embodiment of the present invention shown in FIG. 13, it is possible to increase the inner diameter of the introduction hole 60 at the surface of the channel base 59 opposed to the channel cover 13, thereby making it possible to dispense a liquid into the reaction container 5 at a smaller injection pressure as compared to a case where the introduction hole has a uniform inner diameter.

Although the reaction container plates shown in FIGS. 12 and 13 have the air vent channels 5a and the air vent channels 5b, a second embodiment of the reaction container plate according to the present invention does not always have to include the air vent channels.

Figure 14A:
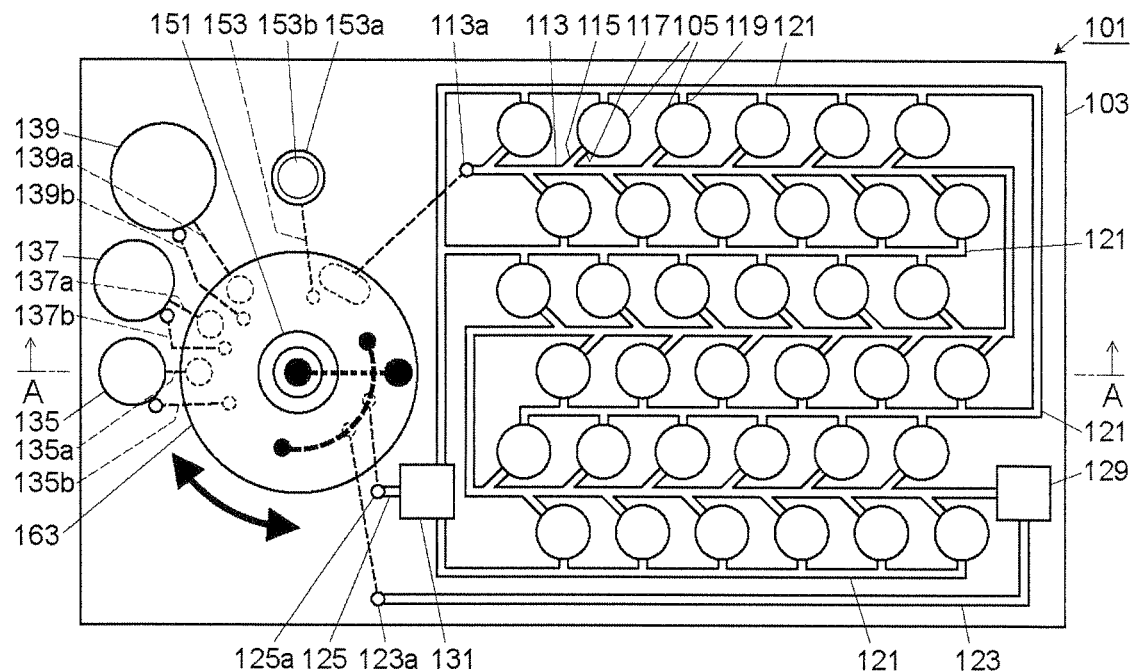
FIG. 14A is a schematic plan view of a reaction container plate according to another embodiment of the present invention.
Figure 14B:
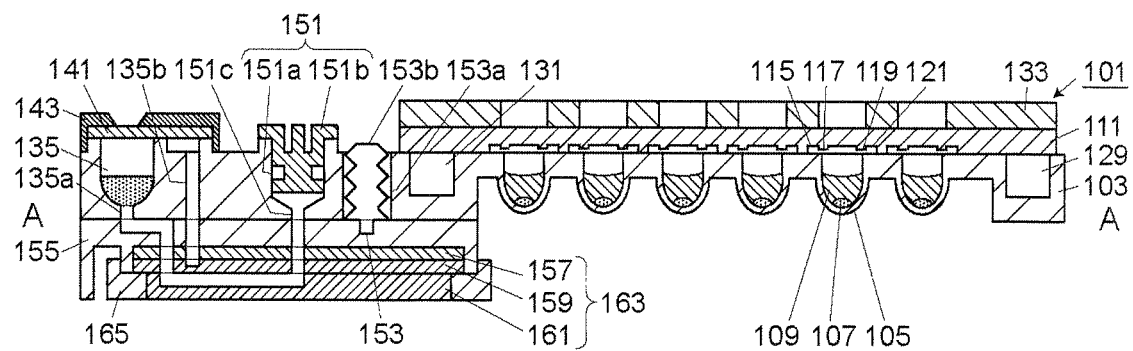
FIG. 14B is a schematic sectional view taken along the A-A line in FIG. 14A, which further includes sectional views of a bellows, drain spaces, a metering channel, an injection channel, and a sample container air vent channel.
Figure 15:
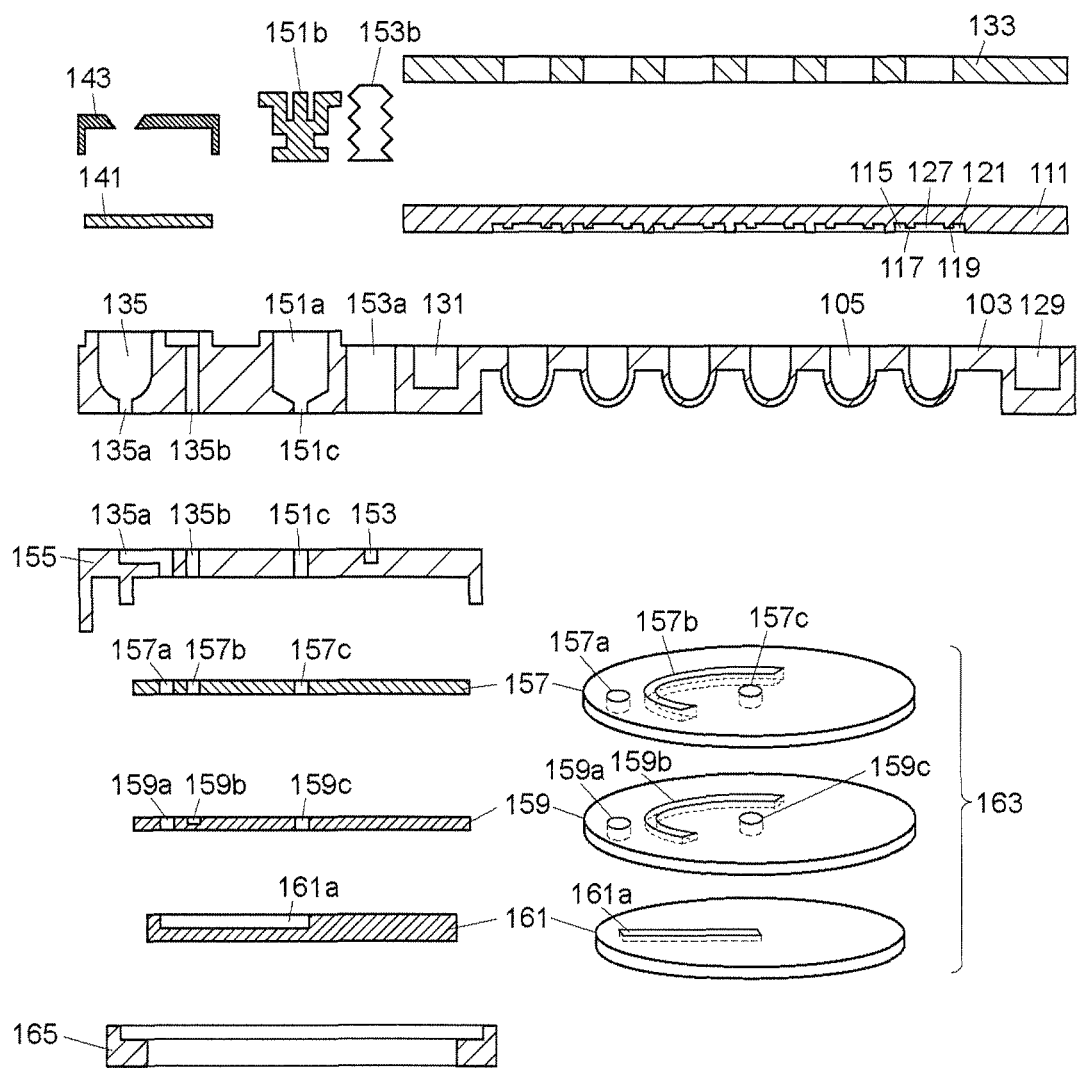
FIG. 15 shows an exploded sectional view of the reaction container plate in the embodiment shown in FIG. 14A and a schematic exploded perspective view of a switching valve.
Figure 16A:
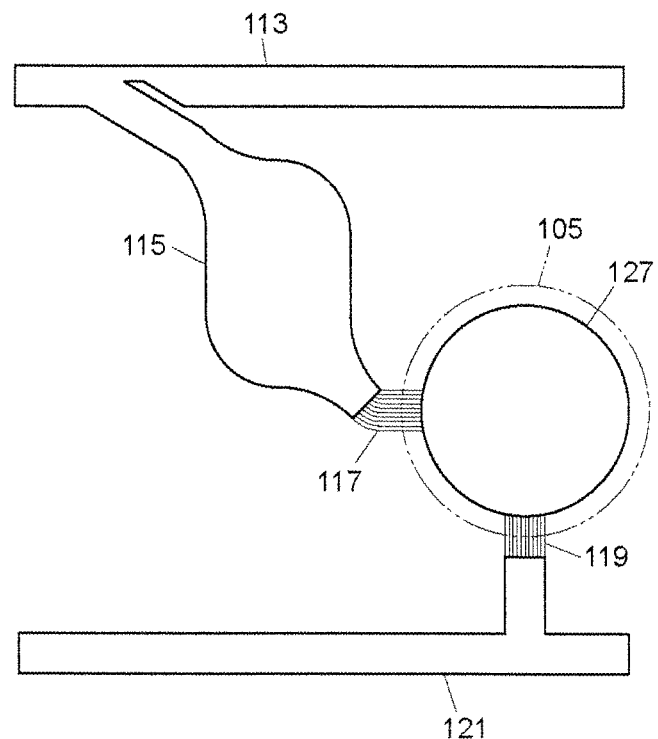
FIG. 16A is a schematic plan view of one reaction container of the reaction container plate in the embodiment shown in FIG. 14A and its vicinity.
Figure 16B:
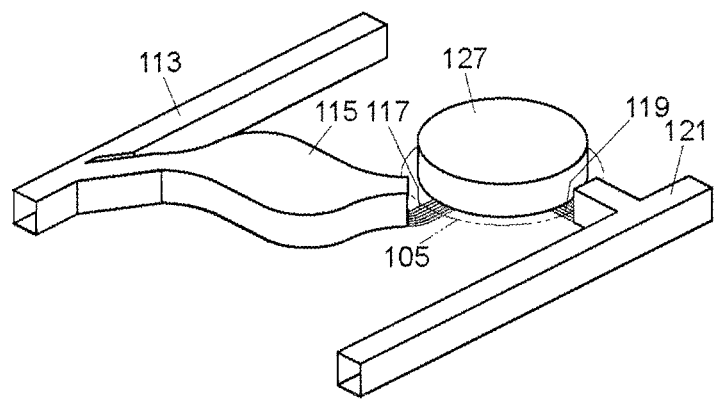
FIG. 16B is a schematic perspective view of one reaction container of the reaction container plate in the embodiment shown in FIG. 14A and its vicinity.
Figure 16C:
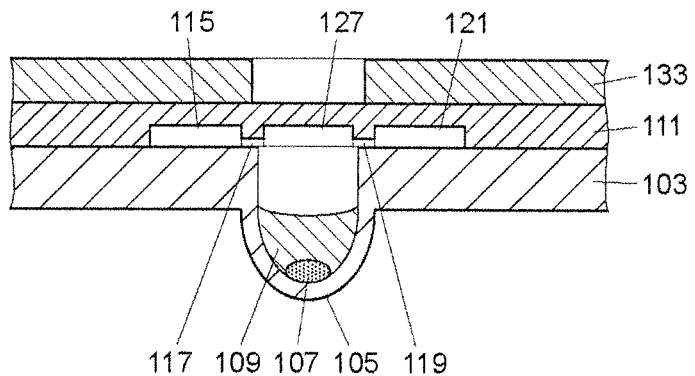
FIG. 16C is a schematic sectional view of one reaction container of the reaction container plate in the embodiment shown in FIG. 14A and its vicinity.
Figure 17A:
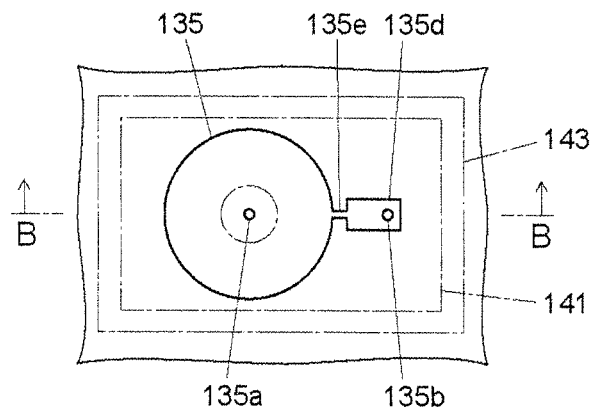
FIG. 17A is an expanded plan view of a sample container of the reaction container plate in the embodiment shown in FIG. 14A.
Figure 17B:
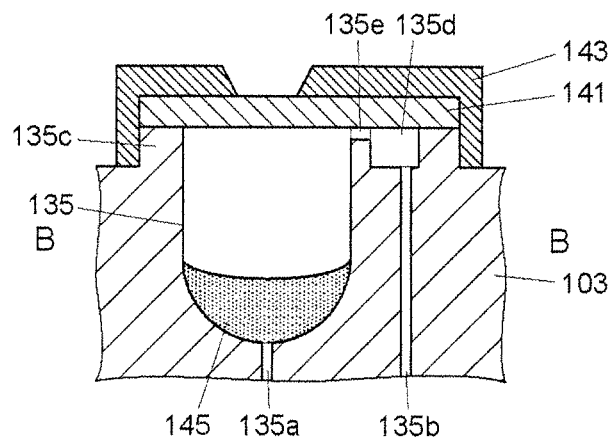
FIG. 17B is a sectional view taken along the B-B line in FIG. 17A.
Figure 18A:
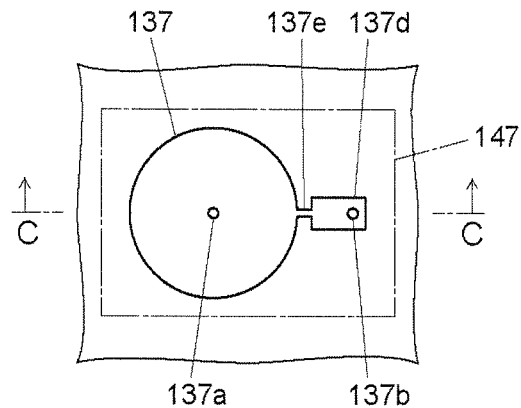
FIG. 18A is an expanded plan view of a reagent container of the reaction container plate in the embodiment shown in FIG. 14A.
Figure 18B:
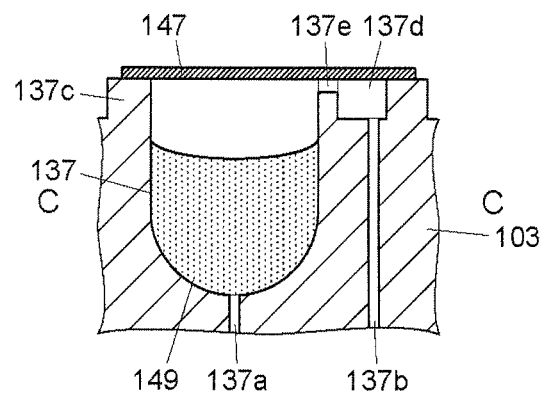
FIG. 18B is a sectional view taken along the C-C line in FIG. 18A.
Figure 19A:
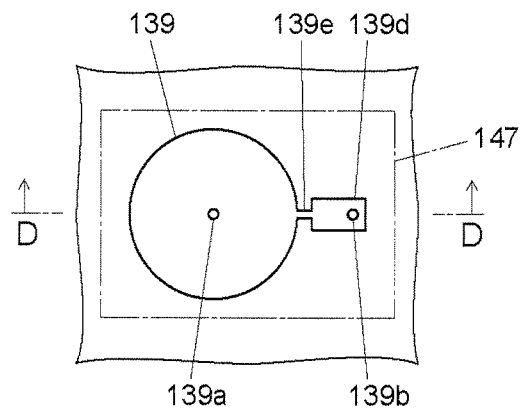
FIG. 19A is an expanded plan view of a container for air suction of the reaction container plate in the embodiment shown in FIG. 14A.
Figure 19B:
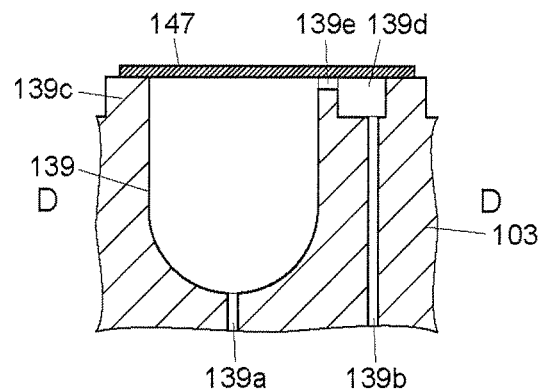
FIG. 19B is a sectional view taken along the D-D line in FIG. 19A.

FIG. 14A is a schematic plan view of yet another embodiment of a reaction container plate, and FIG. 14B is a schematic sectional view taken along the A-A line in FIG. 14A, which further includes the sectional views of a metering channel 115, an injection channel 117, sample container air vent channels 119 and 121, a liquid drain space 129, an air drain space 131, and a bellows 153b. FIG. 15 shows an exploded sectional view of the reaction container plate in the embodiment shown in FIG. 14A and a schematic exploded perspective view of a switching valve. FIGS. 16A to 16C are a schematic plan view, a schematic perspective view, and a schematic sectional view of one reaction container of the reaction container plate in the embodiment shown in FIG. 14A and its vicinity, respectively. FIG. 17A is an expanded plan view of a sample container, and FIG. 17B is a sectional view taken along the B-B line in FIG. 17A. FIG. 18A is an expanded plan view of a reagent container, and FIG. 18B is a sectional view taken along the C-C line in FIG. 18A. FIG. 19A is an expanded plan view of a container for air suction, and FIG. 19B is a sectional view taken along the D-D line in FIG. 19A. With reference to FIGS. 14 to 19, the reaction container plate according to one embodiment of the present invention will be described.

A reaction container plate 101 includes a plurality of reaction containers 105 each having an opening in one surface of a container base 103. In the reaction container plate 1051 according to this embodiment of the present invention, the reaction containers 105 are arranged in an array of 6 rows and 6 columns in a staggered format. In each of the reaction containers 105, a reagent 107 and a wax 109 are contained.

The material of the container base 103 including the reaction containers 105 is not particularly limited. However, in a case where the reaction container plate 101 is intended to be disposable, the material of the container base 103 is preferably a cheaply-available material. Preferred examples of such a material include resin materials such as polypropylene and polycarbonate. In a case where the reaction container plate 101 is intended to be used to detect a substance in the reaction container 105 by absorbance, fluorescence, chemiluminescence, or bioluminescence, the container base 103 is preferably made of an optically-transparent resin so that optical detection can be carried out from the bottom of the reaction container 105. Particularly, in a case where the reaction container plate 101 is intended to be used for fluorescence detection, the container base 103 is preferably made of a low self-fluorescent (i.e., fluorescence emitted from a material itself is weak) and optically-transparent resin, such as polycarbonate. The thickness of the container base 103 is in a range of 0.2 to 4.0 mm, preferably in a range of 1.0 to 2.0 mm. From the viewpoint of low self-fluorescence, the thickness of the container base 103 for fluorescence detection is preferably small.

Referring to FIGS. 14 and 16, a channel base 111 is provided on the container base 103 so as to cover a region where the reaction containers 105 are arranged. The channel base 111 is made of, for example, PDMS (polydimethylsiloxane) or silicone rubber. The thickness of the channel base 111 is, for example, from 1.0 to 5.0 mm. The channel base 111 has a groove in its surface which is in contact with the container base 103. The groove and the surface of the container base 103 together form a main channel 113, the metering channel 115, the injection channel 117, the reaction container air vent channels 119 and 121, and drain space air vent channels 123 and 125. The main channel 113, the metering channel 115, and the injection channel 117 constitute a reaction container channel. In the surface of the channel base 111 which is in contact with the container base 103, a recess 127 is also provided so as to be located above each of the reaction containers 105. It is noted that, in FIG. 14A and FIGS. 16A and 16B, the channel base 111 is not shown, and only the groove and recess provided in the channel base 111 are shown.

The main channel 113 is constituted from one channel, and is therefore bent so as to run in the vicinity of all the reaction containers 105. One end of the main channel 113 is connected to a channel 113a constituted from a through hole provided in the container base 103. The channel 113a is connected to a port of a switching valve 163 (which will be described later).

The other end of the main channel 113 is connected to the liquid drain space 129 provided in the container base 103. The main channel 113 is constituted from a groove having a depth of, for example, 400 μm (micrometers) and a width of, for example, 500 μm. It is noted that a part of the main channel 113 having a predetermined length (e.g., 250 μm) and located downstream of a position, to which the metering channel 115 is connected, has a width smaller than that of the other part of the main channel 113, and the width of such a part is, for example, 250 μm.

The metering channel 115 branches off the main channel 113, and is provided for each of the reaction containers 105. The end of the metering channel 115 on the opposite side from the main channel 113 is located in the vicinity of the reaction container 105. The depth of a groove constituting the metering channel 115 is, for example, 400 μm. The metering channel 115 is designed to have a predetermined internal capacity of, for example, 2.5 μL. A part of the metering channel 115 connected to the main channel 113 has a width, for example, 500 μm, which is larger than that of the above-described narrow part of the main channel 113. Therefore, at a position where the metering channel 115 branches off the main channel 113, the resistance to the flow of a liquid coming from one end of the main channel 113 is larger in the main channel 113 than in the metering channel 115. For this reason, the liquid coming from one end of the main channel 113 first flows into the metering channel 115 to fill the metering channel 115, and then flows downstream through the narrow part of the main channel 113.

The injection channel 117 is also provided for each of the reaction containers 105. One end of the injection channel 117 is connected to the metering channel 115, and the other end of the injection channel 117 is connected to the recess 127 located above the reaction container 105 so as to be led to the space above the reaction container 105. The injection channel 117 is designed to have a size allowing the liquid-tightness of the reaction container 105 to be maintained in a state where there is no difference between the pressure in the reaction container 105 and the pressure in the injection channel 117. According to the present embodiment, the injection channel 117 is constituted from a plurality of grooves, and each groove has a depth of, for example, 10 μm and a width of, for example, 20 μm, and the pitch between the adjacent grooves is, for example, 20 μm, and the thirteen grooves are provided in a region having a width of 500 μm. In this case, the area of an interface between the groove constituting the injection channel 117 and the metering channel 115, that is, the cross-sectional area of the groove constituting the injection channel 117 is 200 μm². The recess 127 has a depth of, for example, 400 μm, and has a circular planar shape smaller than that of the reaction container 105.

The reaction container air vent channel 119 is provided for each of the reaction containers 105. One end of the reaction container air vent channel 119 is connected to the recess 127, which is located above the reaction container 105, at a position different from the position, to which the injection channel 117 is connected, so as to be located above the reaction container 105. The reaction container air vent channel 119 is designed to have a size allowing the liquid-tightness of the reaction container 105 to be maintained in a state where there is no difference between the pressure in the reaction container 105 and the pressure in the reaction container air vent channel 119. The other end of the reaction container air vent channel 119 is connected to the reaction container air vent channel 121. According to the present embodiment, the reaction container air vent channel 119 is constituted from a plurality of grooves, and each groove has a depth of, for example, 10 μm and a width of, for example, 20 μm, and the pitch between the adjacent grooves is, for example, 20 μm, and the thirteen grooves are provided in a region having a width of 500 μm.

The reaction container plate according to the present embodiment has a plurality of reaction container air vent channels 121. To each of the reaction container air vent channels 121, a plurality of reaction container air vent channels 119 are connected. These reaction container air vent channels 121 are provided to connect the reaction container air vent channels 119 to the air drain space 131 provided in the container base 103. Each of the reaction container air vent channels 121 is constituted from a groove having a depth of, for example, 400 μm and a width of, for example, 500 μm.

The drain space air vent channel 123 is provided to connect the liquid drain space 129 to a port of the switching valve 163 (which will be described later). One end of the drain space air vent channel 123 is located above the liquid drain space 129. The other end of the drain space air vent channel 123 is connected to a channel 123a constituted from a through hole provided in the container base 103. The channel 123a is connected to a port of the switching valve 163 (which will be described later). The drain space air vent channel 123 is constituted from a groove having a depth of, for example, 400 μm and a width of, for example, 500 μm.

The drain space air vent channel 125 is provided to connect the air drain space 131 to a port of the switching valve 163 (which will be described later). One end of the drain space air vent channel 125 is located above the air drain space 131. The other end of the drain space air vent channel 125 is connected to a channel 125a constituted from a through hole provided in the container base 103. The channel 125a is connected to a port of the switching valve 163 (which will be described later). The drain space air vent channel 125 is constituted from a groove having a depth of, for example, 400 μm and a width of, for example, 500 μm.

On the channel base 111, a channel cover 133 (not shown in FIG. 14A) is provided. The channel cover 133 is provided to fix the channel base 111 to the container base 103. The channel cover 133 has a through hole formed to be located above each of the reaction containers 105.

Referring to FIGS. 14 and 17, in the container base 103, a sample container 135, a reagent container 137, and a container 139 for air suction are provided at positions other than the positions of a region where the reaction containers 105 are arranged, and the drain spaces 129 and 31. The sample container 135, the reagent container 137, and the container 139 for air suction constitute sealed containers of the reaction container plate according to the present invention.

In the container base 103, a sample channel 135a constituted from a through hole extending from the bottom of the sample container 135 to the back surface of the container base 103 and a sample container air vent channel 135b constituted from a through hole extending from the top surface to the back surface of the container base 103 are provided in the vicinity of the sample container 135. On the container base 103, a projecting portion 135c is provided so as to surround an opening of the sample container 135. In the projecting portion 135c, a sample container air vent channel 135d constituted from a through hole is provided so as to be located above the sample container air vent channel 135b. In the surface of the projecting portion 135c, a sample container air vent channel 135e which allows the sample container 135 to communicate with the sample container air vent channel 135d is provided. The sample container air vent channel 135e is constituted from one or more narrow holes, and each narrow hole has a width of, for example, 5 to 200 μm and a depth of, for example, 5 to 200 μm. The sample container air vent channel 135e is provided to maintain the liquid-tightness of the sample container 135 in a state where there is no difference between the pressure in the sample container 135 and the pressure in the sample container air vent channel 135d. On the projecting portion 135c, a septum 141 as an elastic member to cover the sample container 135 and the air vent channel 135d is provided. The septum 141 is made of an elastic material such as silicone rubber or PDMS. Therefore, a dispensing device having a sharp tip can pass through the septum 141 to form a through hole, but the through hole can be closed by pulling the dispensing device out of the septum 141 due to its elasticity. On the septum 141, a septum stopper 143 for fixing the septum 141 is provided. The septum stopper 143 has an opening located above the sample container 135. According to the present embodiment, a reagent 145 is previously contained in the sample container 135.

As shown in FIG. 18, in the container base 103, a reagent channel 137a constituted from a through hole extending from the bottom of the reagent container 137 to the back surface of the container base 103 and a reagent container air vent channel 137b constituted from a through hole extending from the top surface to the back surface of the container base 103 are provided in the vicinity of the reagent container 137. On the container base 103, a projecting portion 137c is provided so as to surround an opening of the reagent container 137. In the projecting portion 137c, a reagent container air vent channel 137d constituted from a through hole is provided so as to be located above the reagent container air vent channel 137b. In the surface of the projecting portion 137c, a reagent container air vent channel 137e which allows the reagent container 137 to communicate with the reagent container air vent channel 137d is provided.

The reagent container air vent channel 137e is constituted from one or more narrow holes, and each narrow hole has a width of, for example, 5 to 200 μm and a depth of, for example, 5 to 200 μm. The reagent container air vent channel 137e is provided to maintain the liquid-tightness of the reagent container 137 in a state where there is no difference between the pressure in the reagent container 137 and the pressure in the reagent container air vent channel 137d. On the projecting portion 137c, a film 147 made of, for example, aluminum to cover the reagent container 137 and the air vent channel 137d is provided. In the reagent container 137, dilution water 149 is contained.

As shown in FIG. 19, the container 139 for air suction has the same structure as the reagent container 137. That is, in the container base 103, a channel 139a for air suction constituted from a through hole extending from the bottom of the container 139 for air suction to the back surface of the container base 103 and an air vent channel 139b for the container for air suction constituted from a through hole extending from the top surface to the back surface of the container base 103 are provided in the vicinity of the container 139 for air suction. On the container base 103, a projecting portion 139c having air vent channels 139d and 139e for the container for air suction is provided so as to surround an opening of the container 139 for air suction. On the projecting portion 139c, a film 147 made of, for example, aluminum is provided. The container 139 for air suction contains neither a liquid nor a solid, but is filled with air.

Referring to FIGS. 14 and 15, in the surface of the container base 103, a syringe 151 is provided at a position other than positions of a region where the reaction containers 105 are arranged, the drain spaces 129 and 131, and the containers 135, 137, and 139. The syringe 151 is constituted from a cylinder 151a formed in the container base 103 and a plunger 151b placed in the cylinder 151a. In the container base 103, a syringe channel 151c constituted from a through hole extending from the bottom of the cylinder 151a to the back surface of the container base 103 is provided.

In the container base 103, the bellows 153b at a position other than the positions of a region where the reaction containers 105 are arranged, the drain spaces 129 and 131, the containers 135, 137, and 139, and the syringe 151 are also provided. The bellows 153b expands and contracts, and therefore, the internal capacity of the bellows 153b is passively variable. The bellows 153b is placed in, for example, a through hole 153a provided in the container base 103.

Further, a container bottom 155 is attached to the back surface of the container base 103 at a position other than the position of a region where the reaction containers 105 are arranged. In the container bottom 155, an air vent channel 153 is provided at a position allowing the air vent channel 153 to communicate with the bellows 153b. The bellows 153b is connected to the container bottom 155 so as to be in close contact with the surface of the container bottom 155. The container bottom 155 is provided to guide the channels 113a, 123a, 125a, 135a, 135b, 137a, 137b, 139a, 139b, 151c, and 153 to predetermined port positions.

On the surface of the reaction container bottom 155 located on the opposite side from the container base 103, the rotary switching valve 163 is provided. The switching valve 163 is constituted from disk-shaped sealing plate 157, rotor upper 159, and rotor base 161. The switching valve 163 is attached to the container bottom 155 by means of a lock 165.

The sealing plate 157 has a through hole 157a, a through groove 157b, and a through hole 157c. The through hole 157a is provided in the vicinity of the peripheral portion of the sealing plate 157, and is connected to any one of the channels 113a, 135a, 137a, and 139a. The through groove 157b is provided inside the through hole 157a and on a circle concentric with the sealing plate 157, and is connected to at least two of the channels 123a, 125a, 135b, 137b, 139b, and 153. The through hole 157c is provided at the center of the sealing plate 157, and is connected to the syringe channel 151c.

The rotor upper 159 has a through hole 159a, a groove 159b, and a through hole 159c. The through hole 159a is provided at a position corresponding to the through hole 157a provided in the sealing plate 157. The groove 159b is provided in the surface of the rotor upper 159 so as to correspond to the through groove 157b provided in the sealing plate 157. The through hole 159c is provided at the center of the rotor upper 159.

The rotor base 161 has a groove 161a. The groove 161a is provided in the surface of the rotor base 161 to connect the through hole 159a provided in the peripheral portion of the rotor upper 159 and the through hole 159c provided at the center of the rotor upper 159 to each other.

By rotating the switching valve 163, the syringe channel 151c is connected to any one of the channels 113a, 135a, 137a, and 139a, and at the same time, the air vent channel 153 is also connected to at least any one of the channels 123a, 125a, 135b, 137b, and 139b.

The switching valve 163 shown in FIG. 14A is in its initial state where the syringe channel 151c is not connected to any one of the channels 113a, 135a, 137a, and 139a, and the air vent channel 153 is not connected to any one of the channels 123a, 125a, 135b, 137b, and 139b, either.

As described above, the injection channel 117 provided in the reaction container plate 101 is designed so that the liquid-tightness of the reaction container 105 is maintained in a state where there is no difference between the pressure in the injection channel 117 and the pressure in the reaction container 105. The reaction container air vent channel 119 is also designed so that the liquid-tightness of the reaction container 105 is maintained in a state where there is no difference between the pressure in the reaction container 105 and the pressure in the reaction container air vent channel 119. The main channel 113 constituting the reaction container channel, the liquid drain space 129 connected to the main channel 113, and the drain space air vent channel 123 can be hermetically sealed by switching of the switching valve 163. The containers 135, 137, and 139 are sealed with the septum 141 or the film 147. The channels 135a, 135b, 137a, 137b, 139a, and 139b connected to the containers 135, 137, and 139, respectively, can be hermetically sealed by switching the switching valve 163. One end of the air vent channel 153 is connected to the bellows 153b, and therefore, the air vent channel 153 is hermetically sealed. As described above, the containers and channels in the reaction container plate 101 constitute a closed system. It is noted that even in a case where the reaction container plate 101 does not have the bellows 153b and the air vent channel 153 is connected to the atmosphere outside the reaction container plate 101, the air vent channel 153 can be cut off from the containers and the channels other than the air vent channel 153 provided in the reaction container plate 101 by switching of the switching valve 163, and therefore, the containers for containing a liquid and the channels for flowing a liquid can be hermetically sealed.

Figure 20:
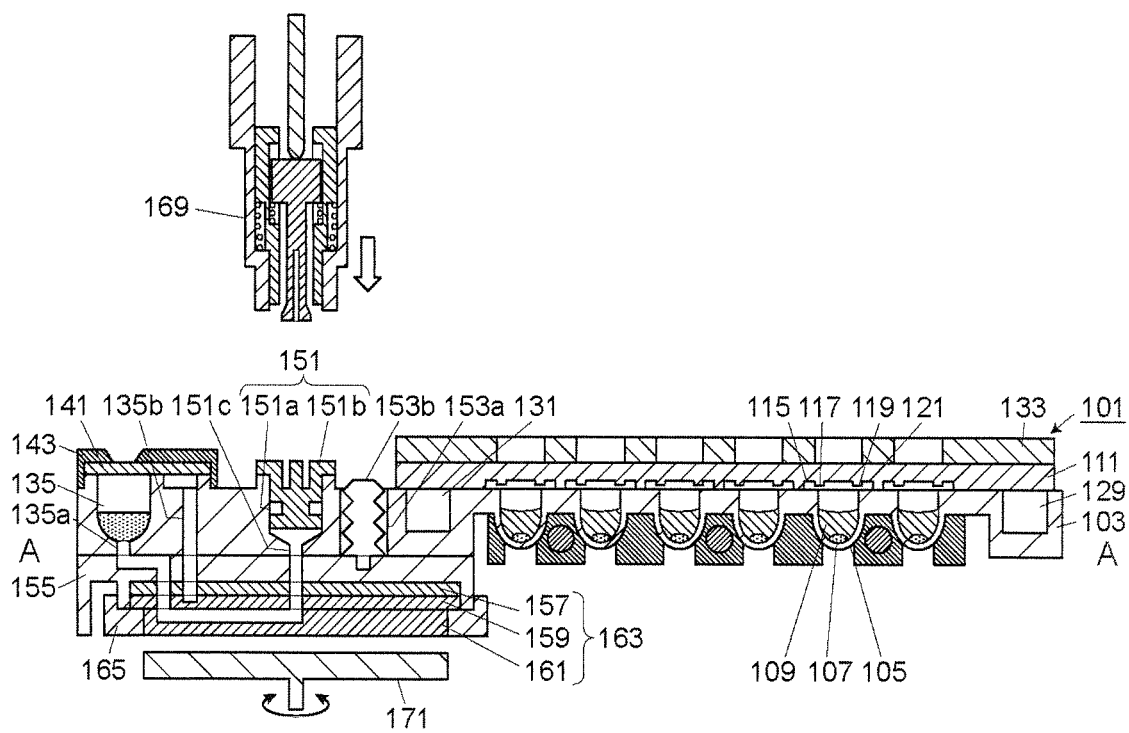
FIG. 20 is a schematic sectional view showing the reaction container plate and a reaction processing apparatus for processing the reaction container plate.

FIG. 20 is a sectional view showing the reaction container plate 101 shown in FIG. 14 and a reaction processing apparatus for processing the reaction container plate 101. The reaction container plate 101 shown in FIG. 20 has the same structure as that shown in FIG. 14, and therefore, the description thereof is omitted.

The reaction processing apparatus includes a temperature control system 167 for controlling the temperature of the reaction containers 105, a syringe driving unit 169 for driving the syringe 151, and a switching valve driving unit 171 for switching the switching valve 163.

FIGS. 21 to 27 are plan views for explaining the operation of introducing a sample liquid into the reaction containers 105 from the sample container 135. This operation will be described with reference to FIGS. 11 and 21 to 27.

A dispensing device having a sharp tip (not shown) is prepared, and the dispensing device is passed through the septum 141 provided on the sample container 135 to dispense, for example, 5 μL of a sample liquid into the sample container 135. After the completion of the dispensing of the sample liquid, the dispensing device is pulled out of the septum 141. By pulling the dispensing device out of the septum 141, a through hole formed in the septum 141 is closed due to the elasticity of the septum 141.

The syringe driving unit 169 is connected to the plunger 151b of the syringe 151, and the switching valve driving unit 171 is connected to the switching valve 163.

Figure 21:
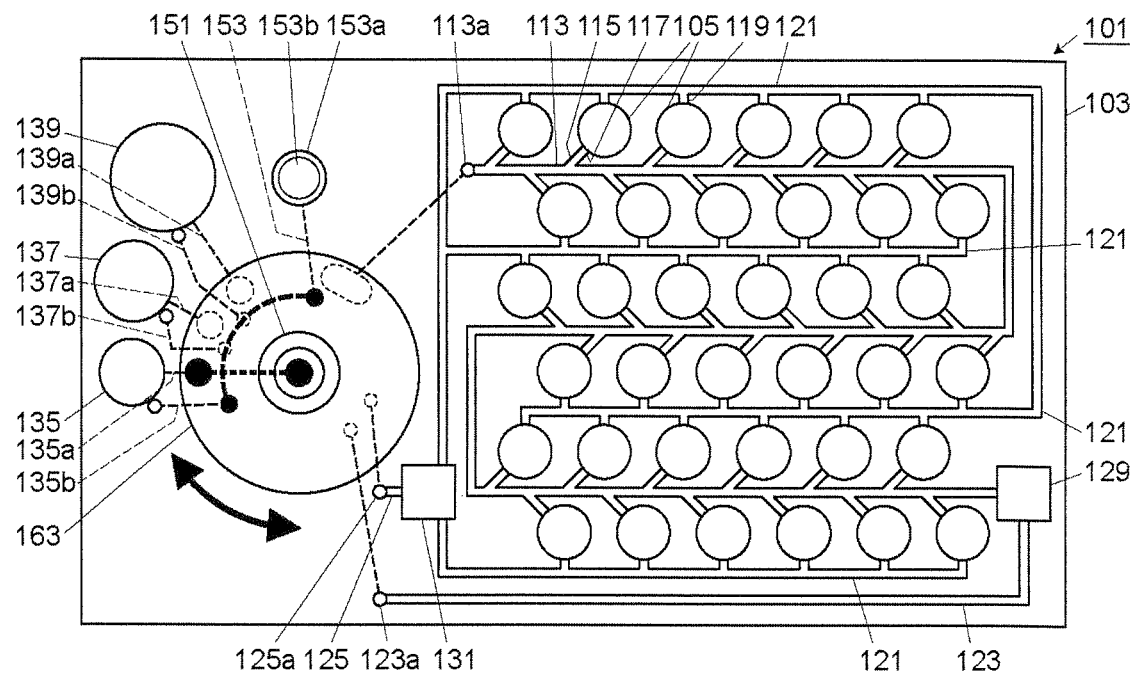
FIG. 21 is a plan view for explaining the operation of introducing a sample liquid into reaction containers from the sample container.

As shown in FIG. 21, the switching valve 163 in its initial state shown in FIG. 14A is rotated to connect the syringe channel 151c to the sample channel 135a and to connect the air vent channel 153 to the sample container air vent channel 135b. At this time, the air vent channels 137b and 139b are also connected to the air vent channel 153. The sample container 135 contains, for example, 45 μL of a reagent 145.

The syringe 151 is slidably moved to mix the sample liquid and the reagent 145 contained in the sample container 135. Then, for example, only 10 μL of the mixture contained in the sample container 135 is sucked into the channel in the switching valve 163, the syringe channel 151c, and the syringe 151. At this time, the bellows 153b expands and contracts with changes in the volume of a gas contained in the sample container 135, since the sample container 135 is connected to the bellows 153b through the air vent channels 135e, 135d, and 135b, the switching valve 163, and the air vent channel 153.

Figure 22:
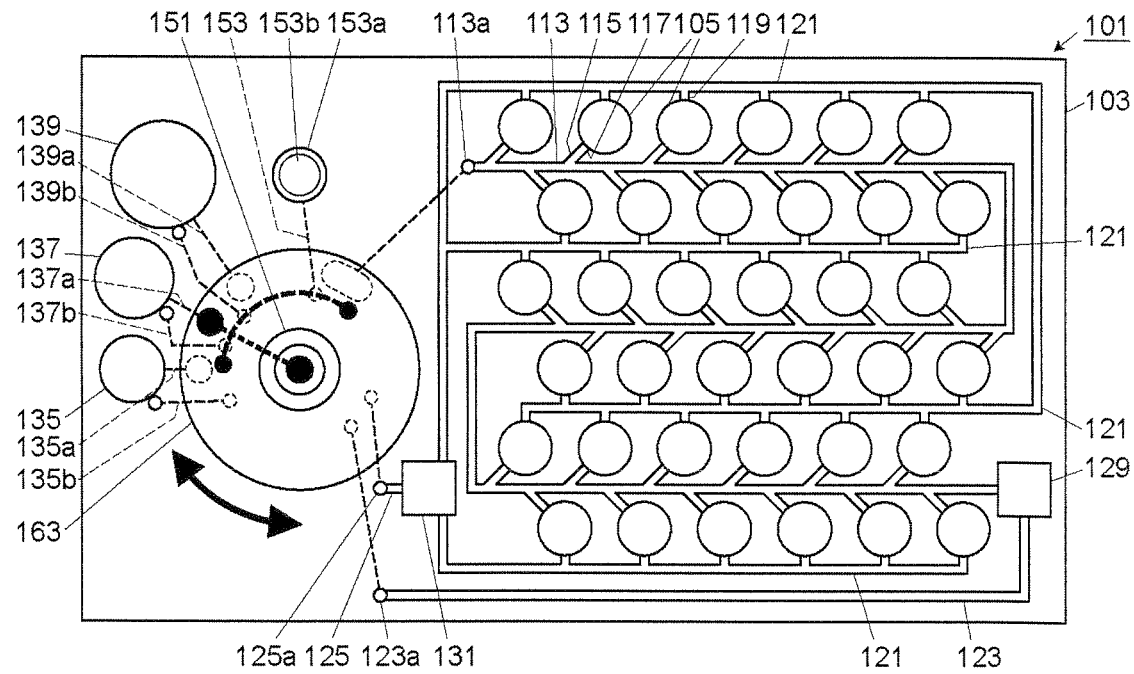
FIG. 22 is a plan view for explaining operation following the operation explained with reference to FIG. 21.

As shown in FIG. 22, the switching valve 163 is rotated to connect the syringe channel 151c to the reagent channel 137a and to connect the air vent channel 153 to the reagent container air vent channel 137b. The reagent container 137 contains, for example, 190 μL of dilution water 149. The mixture sucked into the channel in the switching valve 163, the syringe channel 151c, and the syringe 151 is injected into the reagent container 137. Then, the syringe 151 is slidably moved to mix the mixture and the dilution water 149. For example, the whole diluted mixture, that is, 200 μL of the diluted mixture is sucked into the channel in the switching valve 163, the syringe channel 151c, and the syringe 151. At this time, the bellows 153b expands and contracts with changes in the volume of a gas contained in the reagent container 137, since the reagent container 137 is connected to the bellows 153b through the air drain channels 137e, 137d, and 137b, the switching valve 163, and the air vent channel 153.

Figure 23:
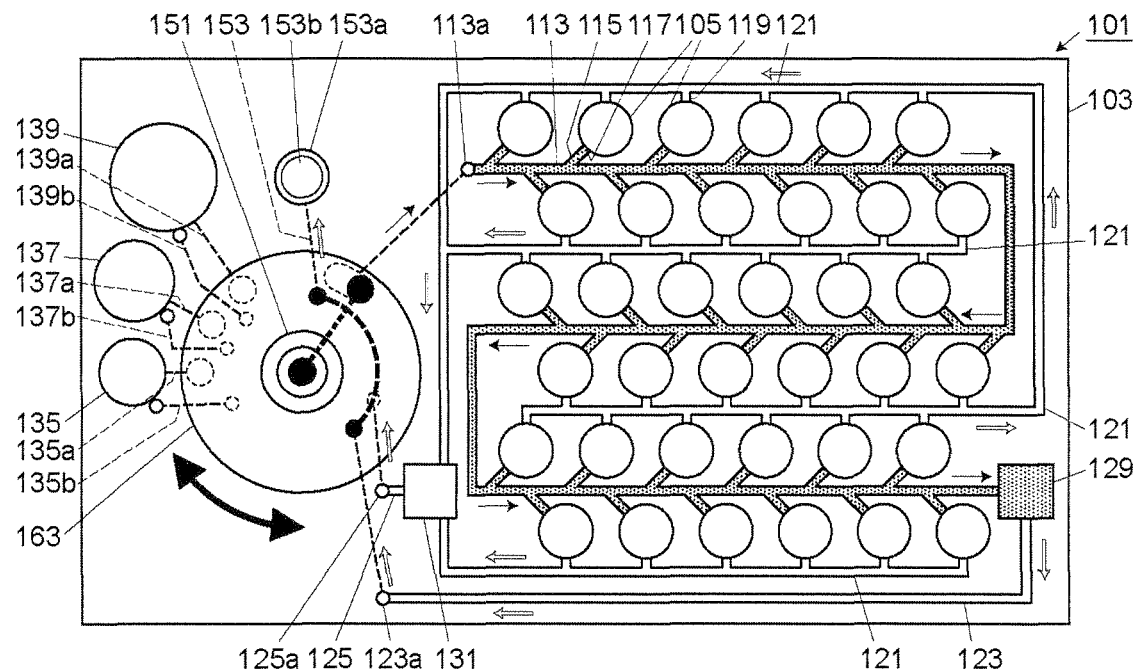
FIG. 23 is a plan view for explaining operation following the operation explained with reference to FIG. 22.

As shown in FIG. 23, the switching valve 163 is rotated to connect the syringe channel 151c to the channel 113a connected to one end of the main channel 113 and to connect the air vent channel 153 to the channels 123a and 125a connected to the liquid drain space 129 and the air drain space 131, respectively. The syringe 151 is driven in an extrusion direction to send the diluted mixture sucked into the channel in the switching valve 163, the syringe channel 151c, and the syringe 151 to the main channel 113. As shown by the arrows and dots in FIG. 23, the diluted mixture injected into the main channel 113 through the channel 113a fills the metering channels 115 one after another in order of increasing distance from the channel 113a, and then reaches the liquid drain space 129. The injection channel 117 allows the passage of a gas but does not allow the passage of the diluted mixture at an introduction pressure applied to introduce the diluted mixture into the main channel 113 and the metering channels 115. When the diluted mixture is introduced into the metering channel 115, a gas contained in the metering channel 115 is transferred into the reaction container 105 through the injection channel 117. Due to the transfer of the gas into the reaction container 105, a gas contained in the reaction container 105 is partially transferred into the reaction container air vent channels 119 and 121. Further, a gas contained in the channels between the reaction container air vent channel 119 and the bellows 153b is sequentially moved toward the bellows 153b (see open arrows in FIG. 23). Furthermore, due to the injection of the diluted mixture into the liquid drain space 129, a gas contained in the channels between the liquid drain space 129 and the bellows 153b is sequentially moved toward the bellows 153b (see open arrows in FIG. 23). As a result, the bellows 153b expands.

Figure 24:
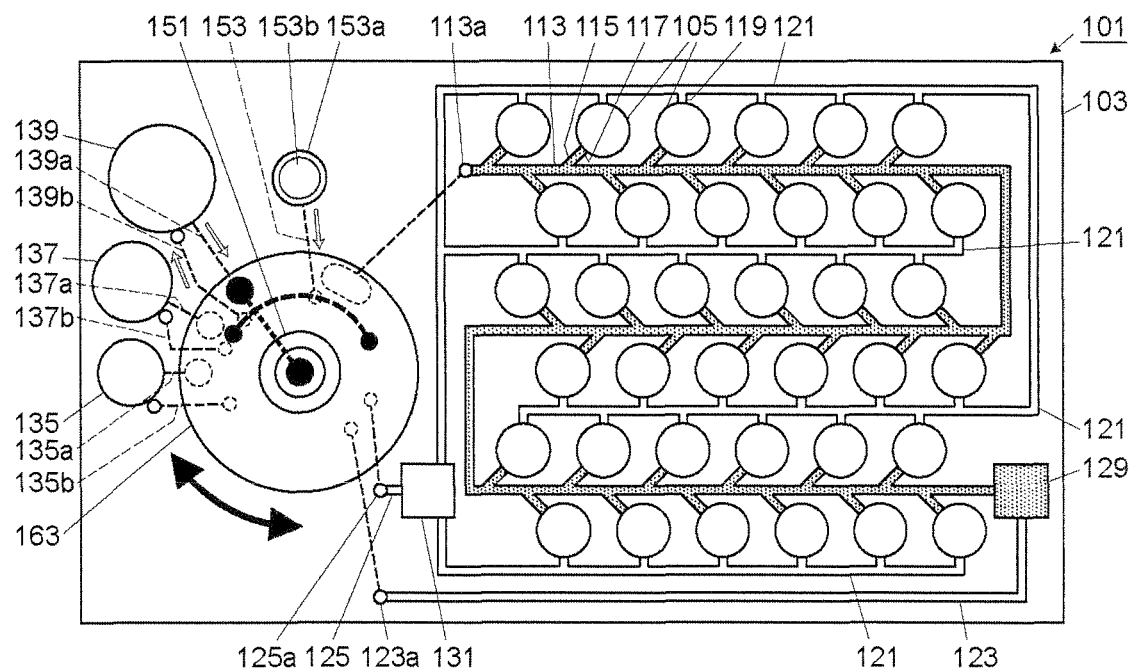
FIG. 24 is a plan view for explaining operation following the operation explained with reference to FIG. 23.

As shown in FIG. 24, the switching valve 163 is rotated to connect the syringe channel 151c to the channel 139a for air suction and to connect the air vent channel 153 to the air vent channel 139b for the container for air suction. Then, the syringe 151 is driven in a suction direction to suck a gas contained in the container 139 for air suction into the channel in the switching valve 163, the syringe channel 151c, and the syringe 151. At this time, the bellows 153b contracts due to the decompression of the container 139 for air suction (see open arrows in FIG. 24), since the container 139 for air suction is connected to the bellows 153b through the air vent channels 139e, 139d, and 139b, the switching valve 163, and the air vent channel 153.

Figure 25:
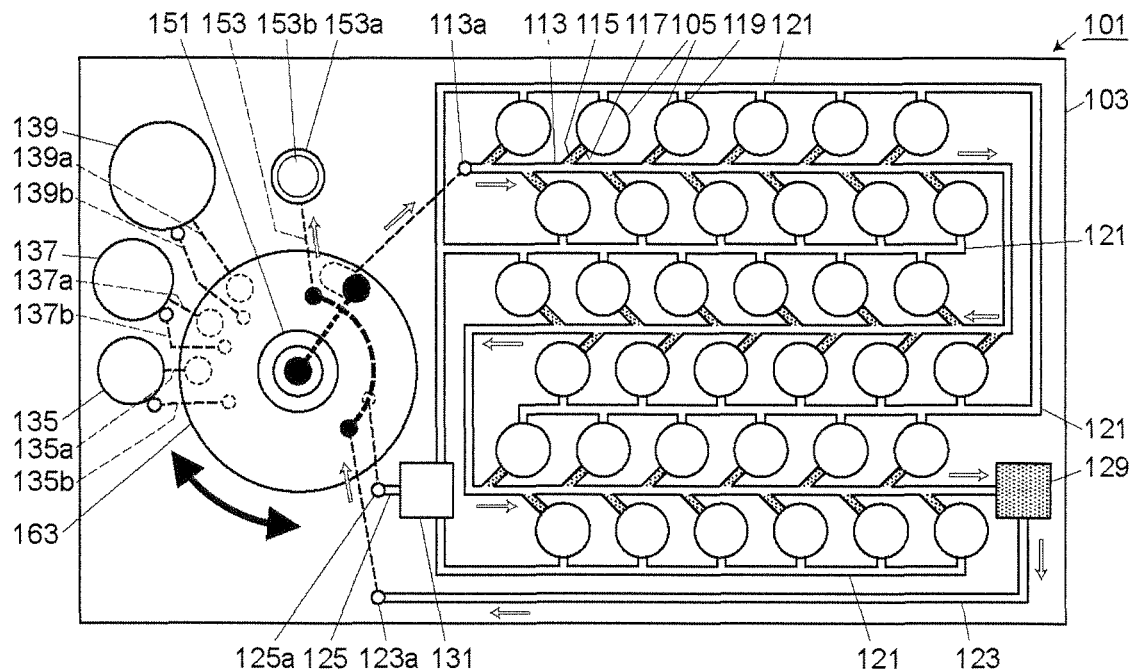
FIG. 25 is a plan view for explaining operation following the operation explained with reference to FIG. 24.

As shown in FIG. 25, the switching valve 163 is rotated to connect the syringe channel 151c to the channel 113a and to connect the air vent channel 153 to the channels 123a and 125a as in the case of a connection state shown in FIG. 23. Then, the syringe 151 is driven in an extrusion direction to send a gas contained in the channel in the switching valve 163, the syringe channel 151c, and the syringe 151 into the main channel 113 to purge the diluted mixture from the main channel 113 (see open arrows in FIG. 25). At this time, the diluted mixture remains in the metering channels 115 (see dots in FIG. 25) because the injection channels 117 do not allow the passage of the diluted mixture at a purge pressure applied to purge the diluted mixture from the main channel 113. The purged diluted mixture is injected into the liquid drain space 129. Further, due to the injection of the diluted mixture into the liquid drain space 129, a gas contained in the channels between the liquid drain space 129 and the bellows 153b is sequentially moved toward the bellows 153b (see open arrows in FIG. 25). As a result the bellows 153b expands.

Figure 26:
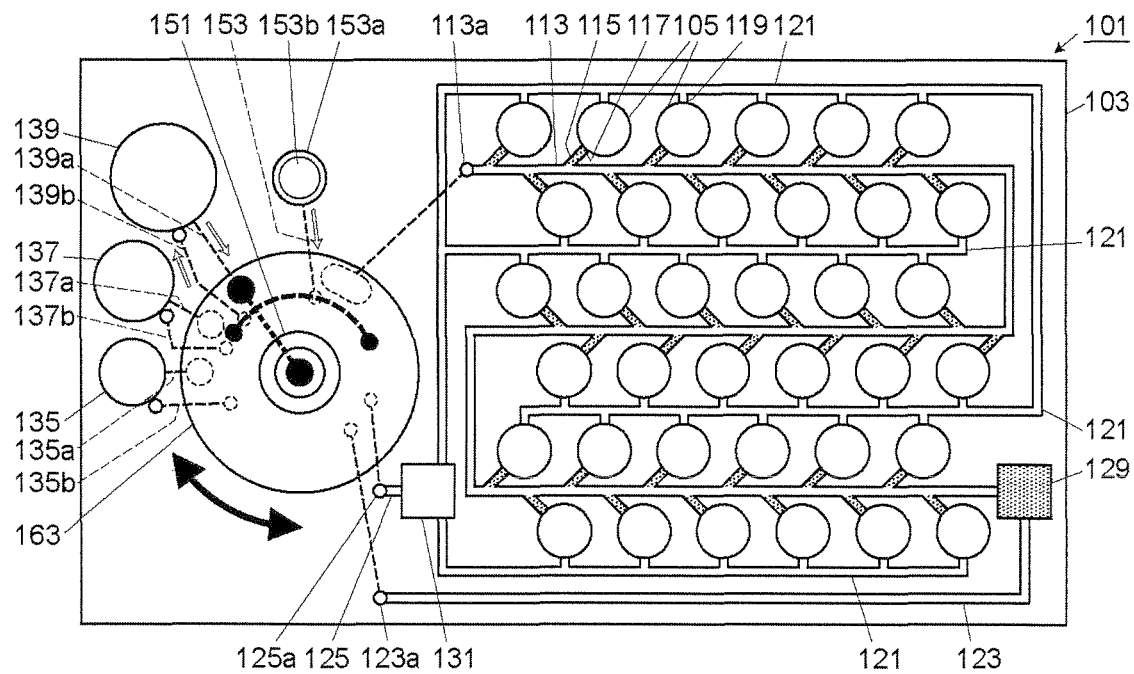
FIG. 26 is a plan view for explaining operation following the operation explained with reference to FIG. 25.

As shown in FIG. 26, the switching valve 163 is rotated to connect the syringe channel 151c to the channel 139a for air suction and to connect the air vent channel 153 to the air vent channel 139b for the container for air suction as in the case of a connection state shown in FIG. 24. Then, the syringe 151 is driven in a suction direction to suck a gas contained in the container 139 for air suction into the channel in the switching valve 163, the syringe channel 151c, and the syringe 151. At this time, as in the case described with reference to FIG. 24, the bellows 153b contracts (see open arrows in FIG. 26).

Figure 27:
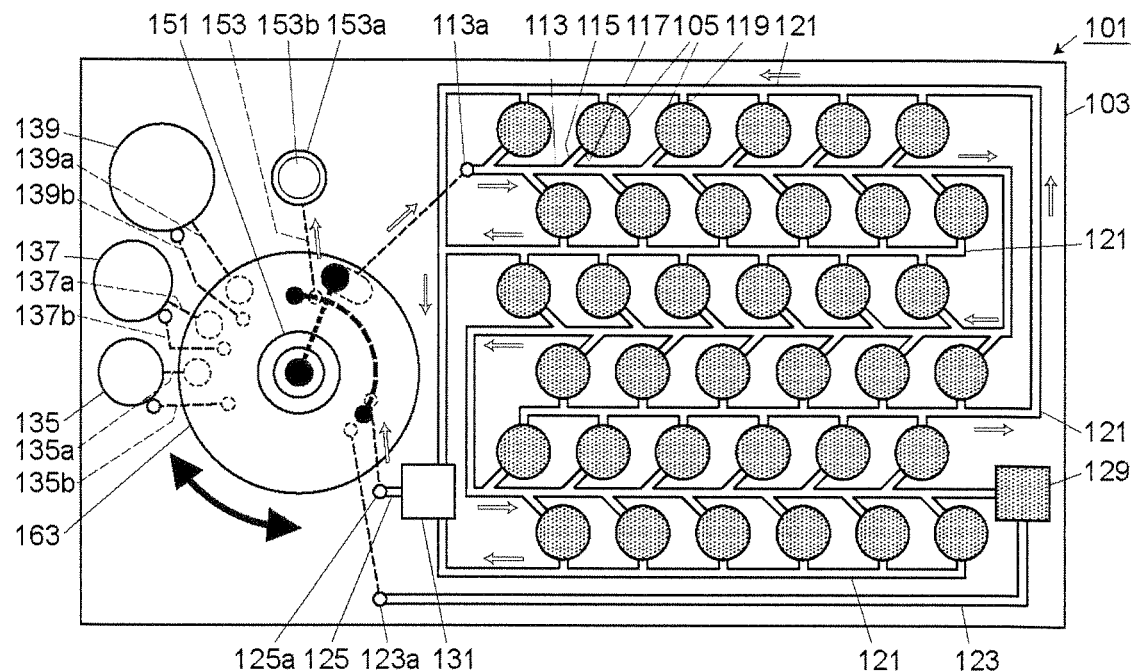
FIG. 27 is a plan view for explaining operation following the operation explained with reference to FIG. 26.

As shown in FIG. 27, the switching valve 163 is rotated to connect the syringe channel 151c to the channel 113a and to connect the air vent channel 153 to the channel 125a. It is noted that the connection state shown in FIG. 27 is different from those shown in FIGS. 23 and 25 in that the liquid drain space 129, to which the downstream end of the main channel 113 is connected, is not connected to the channel in the switching valve 163. Then, the syringe 151 is driven in an extrusion direction. Since the downstream end of the main channel 113 is not connected to the bellows 153b, a pressure larger than the liquid introduction pressure and the purge pressure is applied to the inside of the main channel 113. As a result, the diluted mixture in the metering channels 115 is injected into the reaction containers 105 through the injection channels 117. After the completion of the injection of the diluted mixture into the reaction containers 105, a gas contained in the main channel 113 is partially flown into the reaction containers 105 through the metering channels 115 and the injection channels 117. At this time, a gas contained in the channels between the reaction containers 105 and the bellows 153b is sequentially moved toward the bellows 153b (see open arrows in FIG. 27), since the reaction containers 105 are connected to the bellows 153b through the reaction container air vent channels 119 and 121, the air drain space 131, the drain space air vent channel 125a, and the air vent channel 153. As a result, the bellows 153b expands.

The switching valve 163 is returned to its initial state shown in FIG. 14 to hermetically seal the containers, channels, and drain spaces provided in the reaction container plate 101. Then, the reaction containers 105 are heated by the temperature control system 167 to melt the wax 109. As a result, the diluted mixture injected into each of the reaction containers 105 sinks below the wax 109, and therefore, the diluted mixture is mixed with the reagent 107 so that a reaction occurs. As described above, by using the reaction container plate 101, it is possible to perform reaction processing in a closed system.

Alternatively, the wax 109 may be melted before the injection of the diluted mixture into the reaction containers 105 by heating the reaction containers 105 by the temperature control system 167 so that the diluted mixture is injected into the reaction containers 105 containing the melted wax 109. In this case, the diluted mixture injected into each of the reaction containers 105 immediately sinks below the wax 109, and is then mixed with the reagent 107 so that a reaction occurs. Even when the switching valve 163 is in the connection state shown in FIG. 27, the hermeticity of the reaction container plate 101 is maintained by the bellows 153b. By returning the switching valve 163 to its initial state shown in FIG. 14 after the injection of the diluted mixture into the reaction containers 105, it is possible to hermetically seal the containers, channels, and the drain spaces provided in the reaction container plate 101. It is noted that the switching valve 163 may be returned to its initial state shown in FIG. 14 at any timing during the period from just after the injection of the diluted mixture into the reaction containers 105 until the end of the reaction between the diluted mixture and the reagent 107, or may be returned to its initial state shown in FIG. 14 after the completion of the reaction between the diluted mixture and the reagent 107.

As described above, by using the reaction container plate 101, it is possible to perform reaction processing in a closed system. In addition, it is also possible to maintain the hermeticity of the reaction container plate 101 before and after reaction processing.

According to the present embodiment, grooves for forming the channels 113, 115, 117, 119, 121, and 123 are provided in the channel base 111, but the present invention is not limited to this embodiment. For example, grooves for forming all or part of these channels may be provided in the surface of the container base 103.

Figure 28:
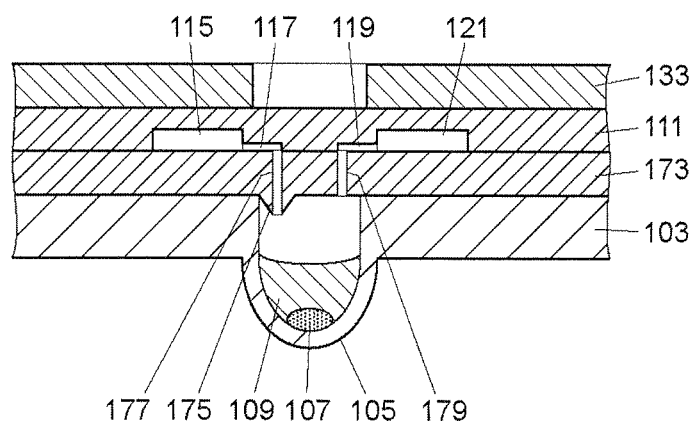
FIG. 28 is an expanded sectional view schematically showing a reaction container of a reaction container plate according to another embodiment of the present invention and its vicinity.

FIG. 28 is an expanded sectional view schematically showing a reaction container of a reaction container plate according to another embodiment of the present invention and its vicinity. The reaction container plate according to the embodiment of the present invention has the same structure as the reaction container plate described above with reference to FIGS. 14 to 27 except that a channel spacer is provided between the container base and the channel base.

On the container base 103, a channel spacer 173 is provided to cover a region where the reaction containers 105 are arranged. On the channel spacer 173, the channel base 111 and the channel cover 133 are further provided in this order. The channel spacer 173 is made of, for example, PDMS or silicone rubber. The thickness of the channel spacer 173 is, for example, 0.5 to 5.0 mm. The channel spacer 173 has a projecting portion 175 projecting into each of the reaction containers 105. The projecting portion 175 is substantially trapezoidal in cross section. For example, the proximal end of the projecting portion 175 has a width of 1.0 to 2.8 mm, and the distal end of the projecting portion 175 has a width of 0.2 to 0.5 mm. That is, the distal end of the projecting portion 175 is narrower than the proximal end of the projecting portion 175. Further, the projecting portion 175 has a super-water-repellent surface. In this regard, it is noted that it is not always necessary to subject the surface of the projecting portion 75 to water-repellent treatment.

Further, in the channel spacer 173, an injection channel 177 is provided at a position corresponding to each of the projecting portions 175. The injection channel 177 is constituted from a through hole extending from the distal end of the projecting portion 175 to the surface of the channel spacer 173 where the projecting portion 175 is not provided. The injection channel 177 has an inner diameter of, for example, 500 μm. The opening of the injection channel 177 provided on the channel base 111 side is connected to the injection channel 117 provided in the channel base 111. It is noted that the reaction container plate according to the embodiment of the present invention is different from the reaction container plate described above with reference to FIGS. 14 to 27 in that the channel base 111 does not have a recess 127.

The channel spacer 173 further has a reaction container air vent channel 179 constituted from a through hole. The reaction container air vent channel 179 is provided to allow the reaction container 105 to communicate with the reaction container air vent channel 119 provided in the channel base 111.

Although not shown in FIG. 28, the channel spacer 173 has through holes at positions corresponding to both ends of the main channel 113, one end of each of the reaction container air vent channels 121 located on the air drain space 131 side, and both ends of each of the drain space air vent channels 123 and 125 to connect these channels 113, 121, 123, and 125 to the containers 129 and 131 provided in the container base 103 and the channels 123a and 125a.

According to the embodiment of the present invention shown in FIG. 28, the end of the injection channel 177 on the opposite side from the injection channel 115 (i.e., the other end of the injection channel) is located at the tip of the projecting portion 175 which projects from the top inner surface of the reaction container 105, and therefore a liquid is easily dropped into the reaction container 105 through the injection channels 115 and 177 when injected into the reaction container 105.

Further, by placing the tip of the projecting portion 175 in the vicinity of the side wall of the reaction container 105 so that when a liquid passes through the injection channel 177 and is then discharged from the tip of the projecting portion 175, a droplet of the liquid formed at the tip of the projecting portion 175 can come into contact with the side wall of the reaction container 105, it is possible to inject the liquid into the reaction container 105 along the side wall of the reaction container 105, thereby making it possible to more reliably inject the liquid into the reaction container 105. However, the projecting portion 175 may be provided at a position which does not allow a droplet formed at the tip of the projecting portion 175 to be brought into contact with the side wall of the reaction container 105.

Figure 29:
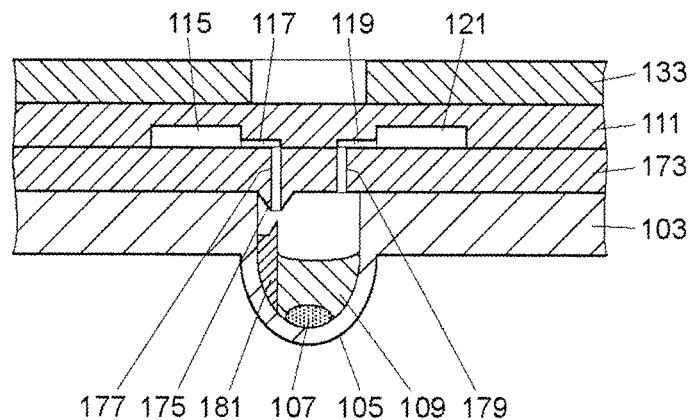
FIG. 29 is an expanded sectional view schematically showing a reaction container of a reaction container plate according to another embodiment of the present invention and its vicinity.

FIG. 29 is an expanded sectional view schematically showing a reaction container of a reaction container plate according to still another embodiment of the present invention and its vicinity. The reaction container plate according to this embodiment is different from the reaction container plate described above with reference to FIG. 28 in that a projecting portion 181 is further provided in the reaction container 105. The tip of the projecting portion 181 is located under the tip of the projecting portion 175. By providing the projecting portion 181, it becomes easy to guide a droplet formed at the tip of the projecting portion 175 into the reaction container 105. The projecting portion 181 becomes particularly effective by subjecting the surface of at least the tip of the projecting portion 181 to hydrophilic treatment.

Figure 30:
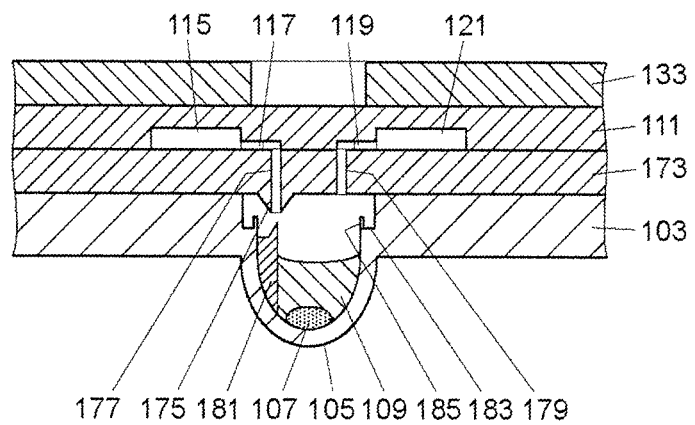
FIG. 30 is an expanded sectional view schematically showing a reaction container of a reaction container plate according to another embodiment of the present invention and its vicinity.

FIG. 30 is an expanded sectional view schematically showing a reaction container of a reaction container plate according to still another embodiment of the present invention and its vicinity.

The reaction container plate according to this embodiment is different from the reaction container plate described above with reference to FIG. 29 in that a stepped portion 183 and a linear projecting portion 185 provided on the top surface of the stepped portion 183 in such a manner that a space is left between the tip of the linear projecting portion 185 and the top surface of the reaction container 105 are further provided. The stepped portion 183 and the linear projecting portion 185 are circular when viewed from above. The tip of the linear projecting portion 185 is provided in such a manner that a space is left between the tip of the linear projecting portion 185 and the side wall of the reaction container 105.

By providing the linear projecting portion 185 in such a manner that a space is left between the tip of the linear projecting portion 185 and the top surface of the reaction container 105 and another space is left between the tip of the linear projecting portion 185 and the side wall of the reaction container 105, it is possible to prevent a liquid contained in the reaction container 105 from reaching the top surface of the reaction container 105 through the side wall of the reaction container 105. The linear projecting portion 185 becomes particularly effective by subjecting the surface of at least the tip of the linear projecting portion 185 to water-repellent treatment.

The stepped portion 183 and the linear projecting portion 185 shown in FIG. 30 can also be applied to the reaction container plate in the embodiment shown in FIG. 28.

In each of these various embodiments described above with reference to FIGS. 28 to 30, grooves for forming the channels 113, 115, 117, 119, 121, and 123 are provided in the channel base 111, but the present invention is not limited to these embodiments. For example, grooves for forming all or part of these channels may be provided in any one of the surfaces of the channel spacer 173 located on the channel base 111 side, the surface of the channel spacer 173 located on the container base 103 side, and the surface of the container base 103.

Although the present invention has been described above with reference to the various embodiments, the present invention is not limited to these embodiments. The shape, material, position, and number of each component in the above description are merely examples, and various changes can be made without departing from the scope of the present invention defined in claims.

For example, the bellows 35b and 153b connected to the air vent channels 35 and 153b respectively may have another structure as long as it is a variable capacity member of which internal capacity is passively variable. Examples of such a bellows having another structure include a bag-shaped one made of a flexible material and a syringe-shaped one.

The reaction container plate according to the present invention does not always need to have a variable capacity member such as a bellows 35b and 153b, and the like.

In a case where a liquid such as a reagent is not previously contained in the container 17, 19, 21, 135, 137, or 139, the air vent channel thereof does not always need to partially have the channel 17e, 19e, 135e, 137e, or 139e constituted from a narrow hole.

In each of the above embodiments, the air vent channels 17b, 19b, 21b, 135b, 137b, and 139b, which communicate with the containers 17, 19, 21, 135, 137, and 139 provided as sealed containers, are connected to the air vent channel 35 and 153 through the switching valve 47, 163, but may be directly connected to the outside of the reaction container plate or a variable capacity part such as bellows 35b and 153b. Further, each of the containers 17, 19, 21, 135, 137, and 139 may be sealed by using an openable and closable cap.

In each of the above embodiments, the container base 3 and 103 are constituted from one component, but may be constituted from two or more components.

The reagent contained in the reaction containers 5 and 105 may be a dry reagent.

It is noted that the sample containers 17, 135 and the reaction containers 5, 105 do not always need to previously contain a reagent.

The container bases 3 and 103 may further have a gene amplification container for carrying out gene amplification reaction. For example, one of the reagent containers 19 and 21 in the examples shown in FIGS. 1 to 13 and the reagent container 137 in the examples shown in FIGS. 14 to 30 may be used as a gene amplification container if they are empty.

By previously placing a reagent for gene amplification reaction in the reaction container 5 and 105, it is possible to carry out gene amplification reaction in the reaction container 5 and 105.

Further, in a case where a liquid to be introduced into the introduction channel 15 and the main channel 113 contains a gene, a probe which reacts with the gene may be previously placed in the reaction container 5 and 105.

The reaction container plate according to the present invention does not always need to have the syringe 33 and 151, and a syringe provided outside the reaction container plate may be used to discharge and suck a liquid or a gas.

In each of the above embodiments, the rotary switching valve 47 or 163 is used as a switching valve. However, a switching valve for use in the reaction container plate according to the present invention is not limited thereto, and various channel switching valves can be used. The reaction container plate according to the present invention may have a plurality of switching valves.

In the embodiments described above with reference to FIGS. 1 to 13, the entire channel cover 13 constitutes a flexible portion of the channel cover of the reaction container plate according to the present invention, but the present invention is not limited to these embodiments. The structure of the channel cover is not particularly limited as long as at least a part of the channel cover constitutes a flexible portion and the flexile portion can be biased toward the channel base to apply an injection pressure to the inside of the introduction channel to inject a liquid contained in the introduction channel into the reaction container through the introduction hole. For example, the channel cover may have a flexible portion made of a flexible material only in a part thereof located above the introduction hole.

In the embodiments described above with reference to FIGS. 1 to 13, the entire channel base 11 is made of an elastic material, but the present invention is not limited to these embodiments. The structure of the channel base 11 is not particularly limited as long as the introduction hole provided in the channel base does not allow the passage of a liquid at an introduction pressure applied to the inside of the introduction channel to introduce the liquid into the introduction channel but allows the passage of the liquid at an injection pressure much higher than the introduction pressure applied to the inside of the introduction channel to inject the liquid contained in the introduction channel into the reaction container. For example, the channel base may have such a structure that only the introduction hole and a portion around the introduction hole are formed from an elastic member.

Further, in the embodiments described above with reference to FIGS. 1 to 13, the biasing system 55 is provided to bias the channel cover 13 toward the channel base 11, but a heating system may be provided instead of the biasing system 55. For example, the second unit 55b shown in FIG. 10 may be a heating system. In this case, as shown in FIG. 10A, an air layer is allowed to be present above the inner space of the introduction channel 15 when the liquid mixture 57 is introduced into the introduction channel 15. Then, as shown in FIG. 10B, the first unit 55a is moved toward the reaction container plate 1 to press the channel cover 13 against the channel base 11 at positions corresponding to the positions of areas around the reaction containers 5. As a result, sealed introduction channel spaces containing the liquid mixture 57 are formed above the introduction holes 11b located above the reaction containers 5. Then, the second unit 55b as a heating system is brought into contact with the channel cover 13 covering the sealed introduction channel spaces. As a result, the sealed introduction channel spaces are heated and the pressure in the sealed introduction channel spaces is increased so that the introduction holes 11b are elastically opened and the liquid mixture 57 is dispensed into the reaction containers 5.

In the embodiments described above with reference to FIGS. 1 to 13, the channel base 11 does not always have to include the projecting portion 11a.

In the embodiments described above with reference to FIGS. 1 to 13, the air vent channel 5a is connected to the drain space 15c through the air vent channel 5b, but the present invention is not limited to these embodiments. The structure of the air vent channel connected to the reaction container is not particularly limited as long as the air vent channel can sufficiently reduce an increase in the pressure in the reaction container caused by introduction of a liquid into the reaction container. It is to be noted that the air vent channel is preferably cut off from an outside atmosphere or hermetically sealable to prevent the entry of foreign matter from the outside of the reaction container plate and the pollution of an environment outside the reaction container plate with the liquid.

In the embodiments described above with reference to FIGS. 14 to 30, the regent container 137 contains dilution water 149, but may contain a reagent instead of the dilution water 149.

In the embodiments described above with reference to FIGS. 14 to 30, the syringe 151 is placed on the switching valve 163. However, the position of the syringe 151 is not limited to a position on the switching valve 163, and the syringe 151 may be placed at any position.

In the embodiments described above with reference to FIGS. 14 to 30, a liquid filling the metering channel 115 is injected into the reaction container 105 through the injection channel 117 by applying a pressure to the inside of the main channel 113 after air purge, but the reaction processing method in the present invention is not limited to such a method. For example, a liquid filling the metering channel 115 may be injected into the reaction container 105 through the injection channel 117 by creating a negative pressure in the reaction container air vent channel 121 and then in the reaction container 105. In this case, it is necessary to change the channel configuration of the reaction container plate so that a negative pressure can be created in the reaction container air vent channel 121 by using the syringe 151. Alternatively, another syringe may be additionally prepared. In this case, a positive pressure is created in the main channel 113 and a negative pressure is created in the reaction container 105 to inject the liquid into the reaction container 105.

In the embodiments described above with reference to FIGS. 14 to 30, one main channel 113 is provided, and all the metering channels 115 are connected to the main channel 113. However, the channel configuration of the reaction container plate according to the present invention is not limited thereto. For example, a plurality of main channels may be provided. In this case, one or more metering channels may be connected to each of the main channels.

In a case where the reaction container plate according to the present invention has the introduction channel 15 or the main channel 113, it is preferred that the introduction channel or the main channel can be hermetically sealed. In this regard, the introduction channel and the main channel may be hermetically sealed by, for example, allowing both ends of the introduction channel or the main channel to be openable and closable. The phrase "allowing both ends of the introduction channel or the main channel to be openable and closable" includes a case where each end of the introduction channel or the main channel is connected to another space, and the end of the 'another space' located on the opposite side from the introduction channel or the main channel is openable and closable. In the above embodiments, such 'another space' corresponds to, for example, the drain space 15c and the drain channel 15b, the channel 113a, or the liquid drain space 129, the drain space air vent channel 123, and the channel 123a.

Further, in a case where the reaction container plate according to the present invention has the reaction container air vent channel, it is preferred that the reaction container air vent channel can be hermetically sealed. In this regard, the reaction container air vent channel may be hermetically sealed by, for example, allowing the end of the reaction container air vent channel located on the opposite side from the reaction container to be openable and closable. The phrase "allowing the end of the reaction container air vent channel located on the opposite side from the reaction container to be openable and closable" includes a case where the end of the reaction container air vent channel located on the opposite side from the reaction container is connected to another space and the end of the 'another space' located on the opposite side from the reaction container air vent channel is openable and closable. In the above embodiments, such 'another space' corresponds to, for example, the drain space 15c and the drain channel 15b or the air drain space 131, the drain space air vent channel 125, and the channel 125a.

In the case of the reaction container plate having the introduction channel and the reaction container air vent channel that can be hermetically sealed such as the embodiments described above with reference to FIGS. 1 to 13, a liquid is introduced into the introduction channel. The liquid is then injected into the reaction containers, and both ends of the introduction channel and one end of the reaction container air vent channel located on the opposite side from the reaction container are closed to hermetically seal the introduction channel and the reaction container air vent channel.

In the case of the reaction container plate having the main channel and the reaction container air vent channel that can be hermetically sealed such as the embodiments described above with reference to FIGS. 14 to 30, a liquid is introduced into the main channel and the metering channels. Next, the liquid is purged from the main channel, and further the liquid remaining in the metering channels is injected into the reaction containers. Both ends of the main channel and one end of the reaction container air vent channel located on the opposite side from the reaction container are closed to hermetically seal the main channel and the reaction container air vent channel.

INDUSTRIAL APPLICABILITY

The present invention can be applied to measurements of various chemical and biochemical reactions.

What is claimed is:
1. A reaction container plate comprising:
a sealed reaction container;
a reaction container channel connected to the reaction container;
a sealed container provided separately from the reaction container;

a sealed container channel connected to the sealed container, a syringe for sending a liquid;

a switching valve for connecting the syringe to the reaction container channel or the sealed container channel; and a sealed container air vent channel of which one end is connected to the sealed container.

2. The reaction container plate according to claim 1, wherein a part of the sealed container air vent channel is constituted from a narrow hole for maintaining the liquid-tightness of the sealed container in a state where there is no difference between the pressure in the sealed container and the pressure in the sealed container air vent channel.

3. The reaction container plate according to claim 1, wherein the other end of the sealed container air vent channel is hermetically sealed by being connected to a variable capacity part of which internal capacity is passively variable.

4. The reaction container plate according to claim 1, further comprising:

a container base constituted from a substrate and having the reaction container of which opening is provided in a surface of the substrate;

a channel base provided on the surface of the container base so as to cover the reaction container to seal the reaction container and having a top surface, a back surface and an introduction hole extending from the top surface to the back surface and located above the reaction container; and a channel cover provided on the channel base and having a hollow space in a surface thereof opposed to the channel base so that an introduction channel passing above the introduction hole is formed from the hollow space and the top surface of the channel base, wherein the reaction container channel is constituted from the introduction channel and the introduction hole, the introduction channel can be hermetically sealed, the introduction hole does not allow the passage of a liquid at an introduction pressure applied to an inside of the introduction channel to introduce the liquid into the introduction channel but allows the passage of the liquid at an injection pressure much higher than the introduction pressure applied to the inside of the introduction channel to inject the liquid contained in the introduction channel into the reaction container, and the channel cover has a flexible portion in at least a part thereof corresponding to a part of the introduction channel, and wherein after the liquid is introduced into the introduction channel, the flexible portion of the channel cover is biased toward the channel base to apply the injection pressure to the inside of the introduction channel to inject the liquid into the reaction container through the introduction hole.

5. The reaction container plate according to claim 4 wherein at least the introduction hole and a portion around the introduction hole in the channel base are constituted from an elastic member, and wherein the introduction hole is elastically closed to such a degree that it does not allow the passage of the liquid at the introduction pressure applied to the inside of the introduction channel but is elastically opened to such a degree that it allows the passage of the liquid at the injection pressure applied to the inside of the introduction channel.

6. The reaction container plate according to claim 4, wherein a part of the introduction hole has an inner diameter smaller than that of the introduction hole at the top surface of the channel base opposed to the channel cover.

7. The reaction container plate according to claim 6, wherein the narrower part of the introduction hole has an inner diameter of 1 μm to 2 mm.

8. The reaction container plate according to claim 4, wherein the container base has a plurality of the reaction containers, and wherein the introduction hole is provided above each of the reaction containers and the introduction channel is provided to pass above a plurality of introduction holes.

9. The reaction container plate according to claim 4, wherein the channel base has a projecting portion which projects from a surface thereof opposed to the reaction container plate into the reaction container, and wherein the projecting portion has a proximal end and a distal end narrower than the proximal end and the introduction hole is provided so as to pass through the projecting portion.

10. The reaction container plate according to claim 1, further comprising a reaction container air vent channel connected to the reaction container, wherein the reaction container channel is constituted from a groove formed in the contact surface between two members bonded together or from the groove and a through hole formed in the member, and includes a main channel, a metering channel branched off the main channel and having a predetermined capacity, and an injection channel of which one end is connected to the metering channel and another end is connected to the reaction container, and wherein the main channel and the reaction container air vent channel can be hermetically sealed, the injection channel is formed narrower than the metering channel, and does not allow the passage of a liquid at a liquid introduction pressure applied to introduce the liquid into the main channel and the metering channel and at a purge pressure applied to purge the liquid from the main channel but allows the passage of the liquid at a pressure higher than the liquid introduction pressure and the purge pressure.

11. The reaction container plate according to claim 10, wherein the contact angle of the injection channel with a water droplet is 90° or larger, and the area of an interface between the injection channel and the metering channel is in a range of 1 to 10,000,000 μm$^2$.

12. The reaction container plate according to claims 10, which comprises a plurality of the reaction containers, wherein the metering channel and the injection channel are provided for each of the reaction containers, and a plurality of the metering channels are connected to the main channel.

13. The reaction container plate according to claim 10, further comprising a projecting portion which projects from a top inner surface of the reaction container and has a proximal end and a distal end narrower than the proximal end, wherein the another end of the injection channel is located at the tip of the projecting portion.

14. The reaction container plate according to claim 1, wherein the sealed container is a sample container for containing a sample liquid.

15. The reaction container plate according to claim 14, wherein the sample container is sealed with an elastic member which allows a dispensing device having a sharp tip to pass through to form a through hole and which also allows the through hole to be closed by pulling out the dispensing device due to its elasticity.

16. The reaction container plate according to claim 15, wherein the sample container previously contains a liquid for pretreating a sample or a reagent.

17. The reaction container plate according to claim 14, further comprising one or more reagent containers, each of which is constituted from the sealed container, other than the sample container, wherein the reagent container previously contains a reagent to be used for the reaction of a sample liquid and is sealed with a film, or has an openable and closable cap so that the reagent can be injected thereinto.

18. The reaction container plate according to claim 14, further comprising a gene amplification container which is constituted from the sealed container and used for carrying out gene amplification reaction.

19. The reaction container plate according to claim 1, wherein the switching valve is a rotary valve.

20. The reaction container plate according to claim 19, wherein the rotary valve has a port to be connected to the syringe at the center of rotation and the syringe is placed on the rotary valve.

21. The reaction container plate according to claim 1, wherein the reaction container is used for carrying out at least any one of color reaction, enzymatic reaction, fluorescence reaction, chemiluminescence reaction, and bioluminescence reaction.

22. The reaction container plate according to claim 1, which is intended to be used for measuring a gene-containing sample, wherein gene amplification reaction is carried out in the reaction container.

23. The reaction container plate according to claim 1, wherein the reaction container is made of an optically-transparent material so that optical measurement can be carried out from the bottom of the reaction container or from above the reaction container.

24. The reaction container plate according to claim 1, wherein when a liquid to be introduced into the reaction container channel contains a gene, the reaction container contains a probe which reacts with the gene.

25. A reaction processing apparatus for processing the reaction container plate according to claim 1, comprising:
a syringe driving unit for driving the syringe; and
a switching valve driving unit for operating the switching valve.

* * * * *